(12) United States Patent
Li et al.

(10) Patent No.: US 10,709,733 B2
(45) Date of Patent: Jul. 14, 2020

(54) NONSURGICAL TECHNIQUES FOR RESTORING TOOTH ENAMEL

(71) Applicant: Regents of the University of Minnesota, Minneapolis, MN (US)

(72) Inventors: Yuping Li, Minneapolis, MN (US); Alex Fok, Plymouth, MN (US); Conrado Aparicio, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 78 days.

(21) Appl. No.: 15/674,901

(22) Filed: Aug. 11, 2017

(65) Prior Publication Data

US 2018/0078577 A1 Mar. 22, 2018

Related U.S. Application Data

(60) Provisional application No. 62/373,908, filed on Aug. 11, 2016.

(51) Int. Cl.
| | |
|---|---|
| *A61K 38/00* | (2006.01) |
| *A61K 33/06* | (2006.01) |
| *A61K 33/42* | (2006.01) |
| *A61P 1/02* | (2006.01) |
| *A61K 38/39* | (2006.01) |
| *A61K 9/00* | (2006.01) |
| *A61K 31/785* | (2006.01) |

(52) U.S. Cl.
CPC ............ *A61K 33/06* (2013.01); *A61K 9/0053* (2013.01); *A61K 31/785* (2013.01); *A61K 33/42* (2013.01); *A61K 38/39* (2013.01); *A61P 1/02* (2018.01)

(58) Field of Classification Search
None
See application file for complete search history.

(56) References Cited

U.S. PATENT DOCUMENTS

| | | | |
|---|---|---|---|
| 5,508,342 A | 4/1996 | Antonucci et al. | |
| 5,525,148 A | 6/1996 | Chow et al. | |
| 7,455,854 B2 | 11/2008 | Gower et al. | |
| 7,514,249 B2 | 4/2009 | Gower et al. | |
| 7,544,496 B2 | 6/2009 | Gower et al. | |
| 7,547,449 B2 | 6/2009 | Gower et al. | |
| 2007/0183984 A1* | 8/2007 | Haas | A23G 3/36 424/48 |
| 2011/0076241 A1* | 3/2011 | Kato | A61K 6/0017 424/52 |

FOREIGN PATENT DOCUMENTS

| | | |
|---|---|---|
| WO | 01041821 A | 6/2001 |
| WO | 03089022 A1 | 10/2003 |

OTHER PUBLICATIONS

Wang et al. Biomacromolecules 2011, 12, 672-680).*
Tejeda-Montes et al. Biomaterials 35 (2014) 8339-8347.*
Cury et al., "Enamel remineralization: controlling the caries disease or treating early caries lesions?," Braz Oral Res, May 12, 2009, 8 pp.
Tung et al., "Amorphous Calcium Phosphates for Tooth Mineralization," Compendium, vol. 25, No. 9, Sep. 2004, 5 pp.
Burwell et al., "Functional Remineralization of Dentin Lesions Using Polymer-Induced Liquid-Precursor Process," Plos One, vol. 7, Issue 6, Jun. 2012, 10 pp.
Huq et al., "New Approaches to Enhanced Remineralization of Tooth Enamel," ResearchGate, published online Aug. 25, 2010, 13 pp.
Hurlbutt., "Caries Management with Calcium Phosphate," Journal of Professional Excellence Dimensions of Dental Hygiene, Oct. 2010, 5 pp.
Farooq et al., "A review of novel dental caries preventive material: Casein phosphopeptide-amorphous calcium phosphate (CPP-ACP) complex," King Saud University Journal of Dental Sciences, available online, Apr. 18, 2013, 5 pp.
Gold., "Fluoride Varnish Products in the U.S. Market," Research and Development, vol. 1, Issue 3, Published in the Journal of Research and Development Aug. 22, 2013, 2 pp.
Li et al., "Biomimetic Mineralization of Recombinamer-Based Hydrogels toward Controlled Morphologies and High Mineral Density," Applied Materials and Interfaces, ACS Publications, Oct. 30, 2015, 9 pp.
Li et al., "Hybrid Nanotopographical Surfaces Obtained by Biomimetic Mineralization of Statherin-Inspired Elastin-Like Recombinamers," Advanced Healthcare Materials, Wiley Online Library, Oct. 3, 2014, 10 pp.
Olszta et al., "A New Paradigm for BioMineral Formation: Mineralization Via an Amorphous Liquid-Phase Precursor Process," Dissertation from The University of Florida, Published 7th Conference on the Chemistry and Biology of Mineralized, vol. 44, Jan. 2003, 157 pp.

(Continued)

*Primary Examiner* — Jeanette M Lieb
(74) *Attorney, Agent, or Firm* — Shumaker & Sieffert, P.A.

(57) ABSTRACT

In some examples, the disclosure relates to a method including applying biomimetic mineralization process to an enamel defect of a tooth, wherein the applied biomimetic mineralization process remineralizes the tooth in the enamel defect. For example, applying a biomimetic mineralization process may include applying a polymer stabilized biomimetic mineralization composition in the area of the enamel defect and matrices, wherein the biomimetic mineralization composition infiltrates into a porosity of the enamel defect and crystalizes to remineralize the enamel defect. An example polymer stabilized biomimetic mineralization composition includes calcium, phosphate, and a polyanionic additive. In some examples, an elastin-like polypeptide (ELP) composition may be deposited on the surface of a tooth over an enamel defect prior to depositing a polymer stabilized biomimetic mineralization composition to form an ELP matrix for the polymer stabilized biomimetic mineralization composition to infiltrate into and then mineralize.

19 Claims, 16 Drawing Sheets

Specification includes a Sequence Listing.

(56) References Cited

OTHER PUBLICATIONS

Reynolds et al., "Fluoride and Casein Phosphopeptide-Amorphous Calcium Phosphate," Journal of Dental Research, Apr. 1, 2008, 6 pp.

Thula-Mata et al., "Remineralization of Artificial Dentin Lesions via Polymer-Induced Liquid-Precursor (PILP) Process," NIH Public Access, May 15, 2014, 10 pp.

Wang et al., "Elastin-Like Polypeptide Based Hydroxyapatite Bionanocomposites," ACS Publications, Jan. 10, 2011, 9 pp.

Li et al., "Biomimetic Mineralization of Recombinamer-Based Hydrogels toward Control Morphologies and High Mineral Density," Applied Materials & Interfaces, ACS Publications, Nov. 25, 2015, 9 pp.

\* cited by examiner

Demineralized/
Remineralized
enamel

Sound
enamel $\Delta Z = 2.37$ (mm vol%)

NONSURGICAL TECHNIQUES FOR RESTORING TOOTH ENAMEL

This applicant claims the benefit of U.S. Provisional Patent Application No. 62/373,908, filed Aug. 11, 2016, which is incorporated herein by reference in its entirety.

REFERENCE TO SEQUENCE LISTING, TABLE OR COMPUTER PROGRAM

The Sequence Listing submitted herewith in a computer readable form (CRF) by electronic submission via EFS-Web as file name Sequence_Listing_ST25_20171127.txt is herein incorporated by reference. The electronic copy of the Sequence Listing was created on Nov. 27, 2017, with a file size of 28,445 bytes.

TECHNICAL FIELD

The disclosure relates to dental care and treatment.

SUMMARY

The disclosure relates to systems and non-surgical techniques for restoring tooth enamel, such as, e.g., restoring the structure, physical, mechanical and/or aesthetic properties of tooth enamel. In some examples, methods and compositions for preventing and treating tooth erosive and carious lesions are described. Such techniques may include the application of a biomimetic mineralization process to remineralize tooth enamel. Application of the biomimetic mineralization process may include the application of a biomimetic mineralization composition, such as, e.g., polymer-stabilized amorphous calcium phosphate composition, in the area of an enamel defect. The applied composition may infiltrate into the porosity of the enamel defect, adsorb on partially dissolved enamel crystallites and then crystalize in a way to remineralize tooth enamel. The remineralization of tooth enamel resulting from the polymer-stabilized calcium phosphate composition may treat enamel defects of the tooth and prevent progression of dental caries.

In some examples, an elastin-like polypeptides (ELP) process may be used in combination with a biomimetic mineralization process to remineralize tooth enamel. The ELP process may include application and infiltration of an ELP composition in the area of an enamel defect, e.g., prior to or with the biomimetic mineralization composition. Once infiltrated, the ELP composition may be crosslinked, e.g., to form matrices in the area of the enamel defect. Subsequently, a biomimetic mineralization composition may be applied and infiltrated into the formed matrices and then crystalized to mineralize the enamel defect.

In one example, the disclosure relates to a method comprising applying a biomimetic mineralization process to an enamel defect of a tooth, wherein the applied biomimetic mineralization process remineralizes the enamel defect.

In another example, the disclosure relates to a method comprising applying an elastin-like polypeptide (ELP) composition in the area of the enamel defect, wherein the applied ELP composition infiltrates into open pores of the enamel defect; cross-linking the applied ELP composition to form matrices; and applying a biomimetic mineralization composition in the area of the enamel defect and matrices, wherein the biomimetic mineralization composition infiltrates into both the porosity of the enamel defect and within the matrices, and crystalizes to remineralize the enamel defect.

The details of one or more examples are set forth in the accompanying drawings and the description below. Other features, objects, and advantages of the disclosure will be apparent from the description and drawings, and from the claims.

DETAILED DESCRIPTION

Figure 1:
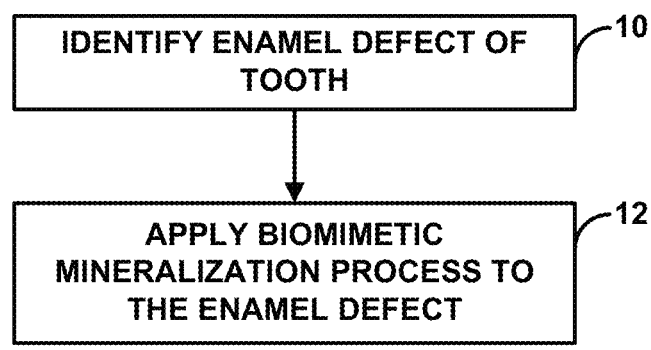
FIG. 1 is a flow diagram illustrating an example technique for restoring enamel of a tooth using a polymer-stabilized calcium phosphate mineralization process.

As described above, disclosure relates to systems and non-surgical techniques for restoring tooth enamel, such as, e.g., restoring the structure, physical, mechanical and/or aesthetic properties of tooth enamel. In some examples, methods and compositions for preventing and treating tooth erosive and carious lesions are described. Such techniques may include the application of a biomimetic mineralization process to remineralize tooth enamel. Application of the biomimetic mineralization process may include the application of a biomimetic mineralization composition, such as, e.g., polymer-stabilized amorphous calcium phosphate composition, in the area of an enamel defect. The applied composition may infiltrate into the porosity of the enamel defect and then crystalize to remineralize the tooth enamel. The remineralization of the tooth enamel resulting from the polymer-stabilized calcium phosphate composition may treat enamel defects of the tooth.

In some examples, an ELP process may be used in combination with a biomimetic mineralization process to remineralize tooth enamel. The ELP process may include application and infiltration of an ELP composition in the area of an enamel defect, e.g., prior to or with the biomimetic mineralization composition. Once infiltrated, the ELP composition may be cross-linked, e.g., to form matrices in the area of the enamel defect. Subsequently, a biomimetic mineralization composition may be applied and infiltrated into the formed matrices and then crystalized to mineralize the enamel defect.

According to the 2005-06 Survey of Dental Services Rendered, an estimated 122.7 million dental restorations were placed in 2006 and the current trends in clinical dentistry indicate that this number is likely to increase. The National Institute of Dental and Craniofacial Research (NIDCR) Strategic Plan of 2009-2013 lists dental caries as the single most common chronic childhood disease in the United States. Over 92% of adults aged 20 to 64 have had dental caries in their permanent teeth, with 26% of them having untreated decay. Traditional approaches of treating dental caries include removing the caries affected enamel or dentin, and replacing it with a restorative material, such as amalgam or resin composites. Such an approach results in a permanent loss of tooth structure.

With an incidence of 49.6% among patients treated with fixed orthodontic appliances, white spot lesions are the most common complication of orthodontic treatment. There are incipient carious lesions, caused by bracket-retained oral bacteria such as *S. mutans* and lactobacillus whose acidic byproducts cause demineralization of enamel crystals. In order to prevent white spot lesions, patients are advised to increase their oral hygiene efforts, receive topical fluoride treatments, and modify their diet to avoid fermentable carbohydrates. However, patient compliance is seen in a mere 13% of those treated. With the speed at which initiation occurs and the potential for cavitation, the unreliability of patient compliance must be countered through alternative methods.

In modern dentistry, non-cavitated caries lesions may be managed non-invasively through remineralization in order to prevent caries progression. Remineralization is a process whereby calcium and phosphate ions are supplied from an external source to the tooth to promote ion deposition into crystal voids in demineralized enamel. Ideally, by using an appropriate remineralization method, the damaged enamel can be repaired in a way that the physical, mechanical and aesthetic properties of enamel are completely restored.

Although fluoride therapy, casein phosphopeptide stabilized amorphous calcium phosphate (Recaldent™), amorphous calcium phosphate (Enamelon™) and bioactive glass (NovaMin™) have been used to enhance remineralization of tooth enamel, they have only demonstrated efficacy in preventing caries formation, but not caries progression.

Enamel caries is the result of progressive subsurface demineralization, ultimately leading to the mechanical failure and cavitation of teeth. The earliest clinical sign of enamel caries is the appearance of a "white spot" lesion on the tooth surface. At this stage, clinicians frequently choose to monitor the lesion appearance, perhaps after the use of topical fluorides, to determine whether or not the lesion will progress, in which case defective tooth tissues will have to be removed and a restoration will be placed to replace tooth defects using dental resin composites or amalgam.

Non-surgical intervention by promoting enamel remineralization or regeneration at the white spot lesion stage would remove the need to "wait and see" and avoid excavation of the tooth to place a restoration. Such non-invasive treatment would represent a major advance in the clinical management of caries diseases.

There are a limited number of remineralization/regeneration products in the market place, e.g., fluoride therapy, casein phosphopeptide stabilized amorphous calcium phosphate (Recaldent™), amorphous calcium phosphate (Enamelon™) and bioactive glass (NovaMin™). All these systems aim to enhance the natural capacity of saliva to remineralize enamel lesions. However, no laboratory or clinical studies have provided sufficient evidence to suggest that the clinical use of these products can effectively prevent lesion progression.

In accordance with some examples of the disclosure, a biomimetic mineralization process may be applied to restore enamel defects of a tooth. The enamel defects (e.g., enamel lesions or erosion) may be the results of calcium and phosphate loss in the enamel due to a drop in the surrounding pH, leaving voids such as interstitial spaces between partially dissolved hydroxyapatite crystallites in the enamel. The biomimetic mineralization process may include depositing a biomimetic mineralization composition including calcium, phosphate, and polyanionic additive in the area of the enamel defect. The polyanionic additive may be configured to stabilize calcium phosphate within the biomimetic mineralization composition to form a liquid-like amorphous calcium phosphate phase on the enamel. With the applied biomimetic mineralization composition, the liquid-like amorphous calcium phosphate can infiltrate (e.g., spontaneously via capillary action and electrostatic attraction) into these interstitial spaces (e.g., nanopores) of the enamel in the area of the defect before crystallization and adsorb on the partially dissolved hydroxyapatite crystallites for regrowth of existing crystallite structures at the area of the enamel defect and restore the enamel.

In some examples, a biomimetic mineralization process may be employed to remineralize the demineralized dentin matrix, i.e. collagen fibrils. In such a process, acidic polymeric additives bind to the calcium ions and form liquid-like amorphous calcium phosphate nanoclusters. Due to their high affinity to collagen and the fluidic character of the biomimetic mineralization, the negatively charged nanoclusters of calcium phosphate precursor may infiltrate into the positively charged regions of the nanoscale gap zones in collagen fibrils by electrostatic attractions, and subsequently solidify into need-like and plate-like hydroxyapatite nanocrystal. The hydroxyapatite nanocrystals formed in collagen fibrils may be about 2 to about 10 nm wide and about 50 to about 200 nm long. Conversely, the composition of enamel is primarily inorganic component (e.g., about 95-98% hydroxyapatite crystals) with about 1-2% of organic components. Human enamel crystallites have roughly hexagonal forms and a cross section of about 30 nm in thickness and about 55 to about 90 nm in width. The enamel crystallites are organized into an ordered structure showing characteristic prismatic pattern. Amelogenin, only found in the early stage of enamel formation, is essential for the organization of enamel rods, control of crystal size and regulation of oriented crystal growth. Surprisingly, despite the different composition of enamel compared to the dentin matrix and lack of amelogenin in the enamel, it has been found that a biomimetic mineralization process may be employed to restore the prismatic structure and hydroxyapatite crystallites of enamel from defects by regrowth of existing crystallite structures.

Figure 2:
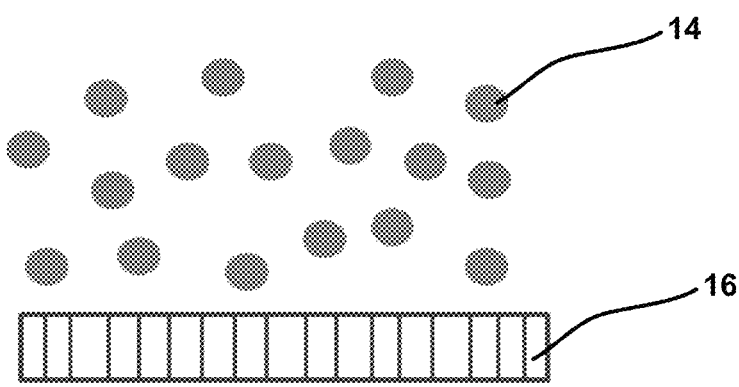
FIG. 2 is a schematic diagram illustrating the example technique of FIG. 1.
Figure 3:
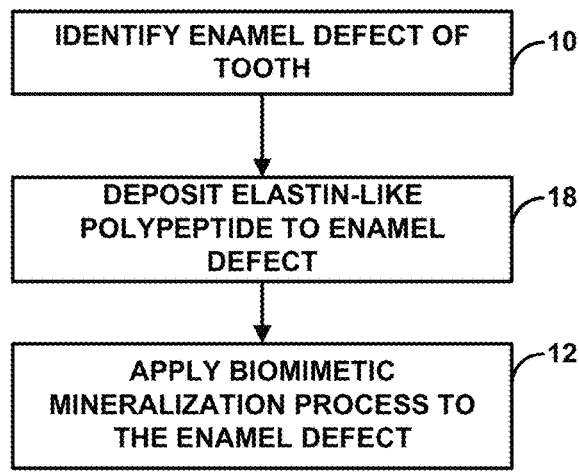
FIG. 3 is a flow diagram illustrating another example technique for restoring enamel of a tooth using a polymer-stabilized calcium phosphate mineralization process.
Figure 4:
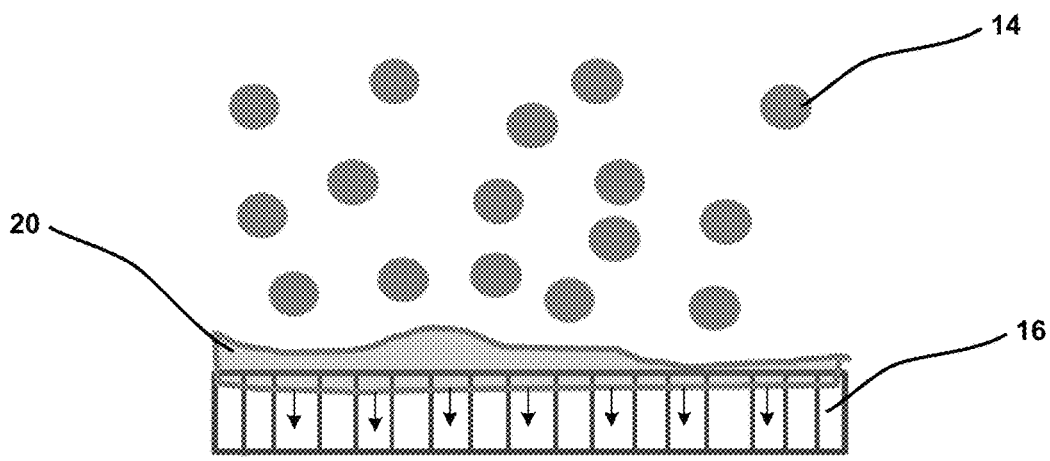
FIG. 4 is a schematic diagram illustrating the example technique of FIG. 3.

FIGS. 1 and 3 are flow diagrams illustrating two example techniques for restoring enamel defects in accordance with examples of the disclosure. The techniques may be used to restore enamel defects of a tooth FIGS. 2 and 4 are conceptual diagrams illustrating the examples techniques of FIGS. 1 and 3, respectively.

As shown in FIGS. 1 and 3, the example techniques may include identifying an area of defect in enamel 16 of a tooth (10). An enamel defect may refer to any enamel deficient regions, such as voids, gaps, erosions, lesions, white spots, recesses or other discontinuities in the enamel caused by mineral loss. An enamel void may refer to any accessible space in enamel caused by ion/mineral loss from the demineralization process.

The enamel defect 16 may be identified (10) using any suitable technique, such as, e.g., visual inspection, cross-polarization optical coherence tomography (CP-OCT), x-ray radiography and the like.

In both the examples of FIGS. 1 and 3, a polymer stabilized biomimetic mineralization process is applied in the area of an enamel defect of a tooth (10). The applied biomimetic mineralization process forms liquid-like amorphous calcium phosphate phase on the enamel 16 in the area of the defect that can spontaneously infiltrate into porous substrates, coalesce, solidify and crystallize, e.g., by regrowing hydroxyapatite nanocrystals.

Application of the biomimetic mineralization process (12) may include deposition of a biomimetic mineralization composition 14 onto the surface of enamel 16 in the area of the defect. The biomimetic mineralization composition 14 may include calcium, phosphate, and polyanionic additive. The polyanionic additive may be configured to stabilize calcium phosphate within the biomimetic mineralization composition to form a liquid-like amorphous calcium phosphate phase on the enamel. With the applied biomimetic mineralization composition, the liquid-like amorphous calcium phosphate can infiltrate into these interstitial spaces of the enamel in the area of the defect before crystallization to remineralize the area of the enamel defect and restore the enamel.

Any suitable biomimetic mineralization composition 14 may be used. Example polyanionic additives that may be present in the composition with the calcium and phosphate include polyaspartate, polyacrylic acid and/or polyvinyl phosphonate. The biomimetic mineralization composition may be in the form of a solution (e.g., as a mouthwash or mouthrinse), gel (e.g., a tooth gel or subgingival gel), dentifrice, or other suitable form. In the case of a solution, water or other liquid may be included with the calcium, phosphate, and polyanionic additives to form a liquid solution. In some examples, the liquid solution may be used as a mouthwash to apply the biomimetic mineralization composition to an area of enamel defect. In other examples, a gel may be formed, e.g., by including one or more viscous polymers with the calcium, phosphate, and polyanionic additives. The gel may be applied in the area of an enamel defect in any suitable manner such as, e.g., carried by a tray or mouth guard that is inserted within the mouth of a patient with enamel defects. As described herein, the applied biomimetic mineralization composition may infiltrate into the porosity of the enamel defect and then crystalize.

Suitable biomimetic mineralization processes and biomimetic mineralization compositions for mineralization may include one or more examples describes in U.S. Pat. Nos. 7,544,496 and 7,547,449. The entire content of U.S. Pat. Nos. 7,544,496 and 7,547,449 is incorporated herein by reference.

In some examples, remineralization may be performed using a biomimetic mineralization composition containing about 4.2 mM dipotassium phosphate, about 9 mM calcium and about 50 μg/ml of polyaspartic acid. The remineralization composition may be in various forms including mouthrinse or mouthwash, tooth gel, and subgingival gel.

In the example technique of FIG. 1, the biomimetic mineralization process may be applied (12) without the deposition of the ELP to the enamel defect, e.g., to remineralize early state lesions (e.g., in the form of subsurface caries or white spots). In the example technique of FIG. 3, ELPs may be deposited (18) in combination with the applied biomimetic mineralization process (12), e.g., to remineralize more significant lesions or other enamel defect such as those caused by erosion, as shown in FIG. 4. The applied ELP composition 20 may infiltrate into open pores and other voids in the enamel defect 16 (as represented by the arrows shown in FIG. 4) and then be cross-linked to form a matrix structure. The concept of using ELPs to remineralize such large enamel defects is that ELPs can first fill up the large voids/gaps on the enamel surface in the area of the defect, and the liquid-like amorphous calcium phosphate can then spontaneously infiltrate into the ELP matrices as well as the interstitial spaces between the hydroxyapatite crystallites. In some example, by inducing mineralization using the ELPs, the enamel defects can be filled with minerals that could not be achieved by the biomimetic mineralization process alone.

The elastin-like polypeptides contain the pentapeptide repeat sequence (VPGXG), where V is valine, P is proline, G is glycine, with X being isoleucine, valine or lysine. Elestin-like recombinamers (ELRs) or short elastin-like polypeptides are examples of an ELP. In some examples, ELPs refer to a type of synthetic polypeptides that include hydrogels, self-assembled nanofibrils, films and electron-spun fibers.

The size of the elastin-like polypeptides that can be used in the methods of the disclosure is not specifically limited. Preferably, the peptides will have a size of about 5-800 amino acids. Example elastin-like polypeptides include IK24 (SEQ ID NO: 1), VK24 (SEQ ID NO: 2), REDV (SEQ ID NO: 3), HSS1 (SEQ ID NO: 4), and HSS3 (SEQ ID NO: 5). In a particularly preferred embodiment, the elastin-like polypeptide has a length of 791 amino acids (HSS3). The elastin-like polypeptides may be prepared by any suitable method that is commonly known in the field of peptide synthesis. For example, peptides with a length of more than 50 amino acids may be prepared by recombinant methods. Smaller elastin-like polypeptides are usually prepared by chemical synthesis. For example, the peptides may be chemically synthesized by solid phase or liquid phase methods.

(SEQUENCE ID NO: 1)
MESLLP-((VPGIG)$_2$(VPGKG)(VPGIG)$_2$)$_{24}$-V (SEQUENCE ID NO: 2)
MESLLP-((VPGVG)$_2$(VPGKG)(VPGVG)$_2$)$_{24}$-V (SEQUENCE ID NO: 3)
MESLLP-[(VPGIG)$_2$(VPGKG)(VPGIG)$_2$EEIQIGHIPREDVDYH

LYP(VPGIG)$_2$(VPGKG)(VPGIG)$_2$(VGVAPG)$_3$]$_{10}$-V (SEQUENCE ID NO: 4)
MESLLP-[((VPGIG)$_2$(VPGKG)(VPGIG)$_2$)$_2$DDDEEKFLRRIGR

FG((VPGIG)$_2$VPGKG(VPGIG)$_2$)$_2$]$_3$-V (SEQUENCE ID NO: 5)
MESLLP[((VPGIG)$_2$(VPGKG)(VPGIG)$_2$)$_2$DDDEEKFLRRIGRF

G((VPGIG)$_2$(VPGKG)(VPGIG)$_2$)$_2$]$_3$(VPAVG)$_{20}$[((VPGIG)$_2$ (VPGKG)(VPGIG)$_2$)$_2$DDDEEKFLRRIGRFG((VPGIG)$_2$(VPGKG)

(VPGIG)$_2$)$_2$]$_3$-V

The peptides for use in the methods of the disclosure may comprise any natural proteinogenic amino acid. In addition, the peptides may also be functionalized with alkyne and azide groups using conventional chemical technique to introduce the reactivity required to carry out click chemistry.

HSS3 (or other ELP) may be applied to an enamel defect as an ELP composition using any suitable technique. The applied ELP composition may infiltrate into open pores and other voids in the enamel defect and then be cross-linked to form a matrix structure. The biomimetic mineralization composition may then infiltrate into the ELP matrices and crystalize within the matrices to remineralize the enamel defect.

In some examples, ELPs may display a disordered and hydrated structure at low temperature but may self-assemble into an ordered superstructure at the temperature above its inverse transition temperature. The ELPs may be dissolved into distilled water at concentrations of 5-100 mg/ml to form an ELP composition. In some examples, the ELPs are applied onto air-dried enamel defects with a brush and infiltrated into enamel defects by capillary action. A single application or multiple applications of ELPs may be performed depending on enamel lesion depths. This process may take, e.g., 2 to 5 minutes and air drying may be used to remove excess water. After infiltration into the porous structure of the enamel defect, the ELPs may be chemically cross-linked using glutaraldehyde aqueous solution with the concentration from about 2 to about 10 wt % for 1 to 5 minutes. Excess glutaraldehyde is removed by rinsing with distilled water. Any suitable technique may be utilized to cross-link the ELPs after infiltration.

The examples techniques of FIGS. 1-4 may be employed to treat enamel defects by restoring the enamel. For example, a biomimetic mineralization composition (e.g., solution/paste) may be directly used or placed in a tray/mouth-guard and/or an elastin-like polypeptide composition (e.g., solution/gel) may be applied directly on an enamel defect for: 1) non-invasive treatment of non-cavitated caries lesions; 2) remineralization of enamel white spot lesions, damaged enamel and early caries; 3) regeneration of tooth enamel; 4) improvement of aesthetic appearance (translucence) of anterior teeth; 5) replacement of current porcelain veneers and composite resin in the restoration of shape, color and function of enamel; and/or 6) repairing cracked/chipped teeth.

Application of the biomimetic mineralization composition (e.g., solution/paste) on enamel defects may directly prevent the progression of enamel caries. In some examples, a user may gargle with a gel/paste containing the biomimetic mineralization calcium phosphate clusters for enamel remineralization.

Examples of the disclosure may allow for one or more advantages. In some examples, techniques of the disclosure may be used to treat non-cavitated caries lesions (or other enamel defects) non-invasively through remineralization in an attempt to prevent disease progression and improve aesthetics, strength, and function of damaged enamel. By using the biomimetic mineralization process, (e.g. with elastin-like polypeptides for larger enamel defects), enamel lesions can be remineralized in a way that the structure, composition and mechanical properties, as well as aesthetic appearance of intact enamel can be restored. In some examples, such techniques may be more effective in preventing caries progression than other available techniques. By effectively treating non-cavitated enamel lesions, permanent tooth damage followed by conventional "drill and fill" restoration using artificial substitutes can be avoided.

Examples of the disclosure may relate to the concept of using a liquid-like amorphous calcium phosphate precursor phase to prevent enamel lesion progression by remineralizing enamel defects caused by oral challenges and/or clinical treatment (orthodontic treatment, tooth whitening, etc.).

Examples of the disclosure may include the use of the polymer-stabilized biomimetic mineralization process to recover the physical, mechanical and aesthetic properties of enamel from enamel defects. For example, using a supersaturated polymer-stabilized calcium phosphate phase may 1) induce remineralization of demineralized enamel through the spontaneous infiltration of liquid-like amorphous calcium phosphate clusters into the voids which then solidify into hydroxyapatite crystals; 2) restore the structure of enamel rods and mineral density at demineralized regions; and/or 3) be used as a remineralization method to prevent the progression of early caries lesions.

Examples of the disclosure may include the use of elastin-like polypeptides in combination with the polymer stabilized biomimetic mineralization process, e.g., to restore large enamel defects compositionally, structurally, mechanically and aesthetically. For example, using elastin-like polypeptides in combination with a biomimetic mineralization process can 1) promote enamel lesion remineralization; and/or 2) restore the structure, composition and aesthetics appearance of enamel from late-stage enamel lesions.

As mentioned above, a variety of techniques may be used to treat enamel defects. Fluoride varnishes have been used for lesion prevention for over 50 years, but its ability to remineralize existing lesions is limited by the availability of calcium and phosphate ions from saliva. Fluoride retention and enamel remineralization is highly compromised under hyposalivation conditions. It has been demonstrated that remineralization of enamel using topical fluoride produced predominantly surface remineralization which does little to the aesthetics and structural properties of deeper lesions.

The amorphous calcium phosphate (ACP) technology has been developed and commercialized for enamel remineralization. It is based on unstable amorphous calcium phosphate, where a calcium salt and a phosphate salt are delivered separately or delivered together in a product with a low water activity. In the oral environment, the ACP becomes unstable and rapidly transforms into a thermodynamically stable hydroxyapatite phase. In most cases, it promotes the formation of dental calculus instead of real enamel remineralization.

A remineralization technology, based on casein phosphopeptide-stabilized amorphous calcium phosphate complexes CPP-ACP [Recaldent® CASRN69134-49-5] and casein phosphopeptide-stabilized amorphous calcium fluoride phosphate complexes CPP-ACFP, has been incorporated into commercial sugar-free chewing gum [Trident Xtra Care (Americas), Recaldent (Japan)] and dental cream [Tooth Mousse and Tooth Mousse Plus (Europe and Australia), MI Paste and MI Paste Plus (Japan and Americas)]. Studies on the aforementioned complexes demonstrated that they can only slow the progression of caries but not promote remineralization.

It is believed that no laboratory or clinical studies have provided sufficient evidence to prove that the use of the products mentioned above can restore/regenerate enamel structurally and aesthetically. The main issue for these products is that calcium and phosphate ions used for remineralization come from saliva and, therefore, are usually low in concentration, making the remineralization process very slow. Indeed, it takes years to fully remineralize enamel subsurface lesions by a fluoride treatment in vivo. Although casein phoshopeptides can stabilize ACP, appropriate concentration and phase of the minerals that can induce enamel remineralization may not be formed due to 1) the interference of saliva in oral conditions; 2) efficiency of CPP on stabilization of ACP.

Figure 5:
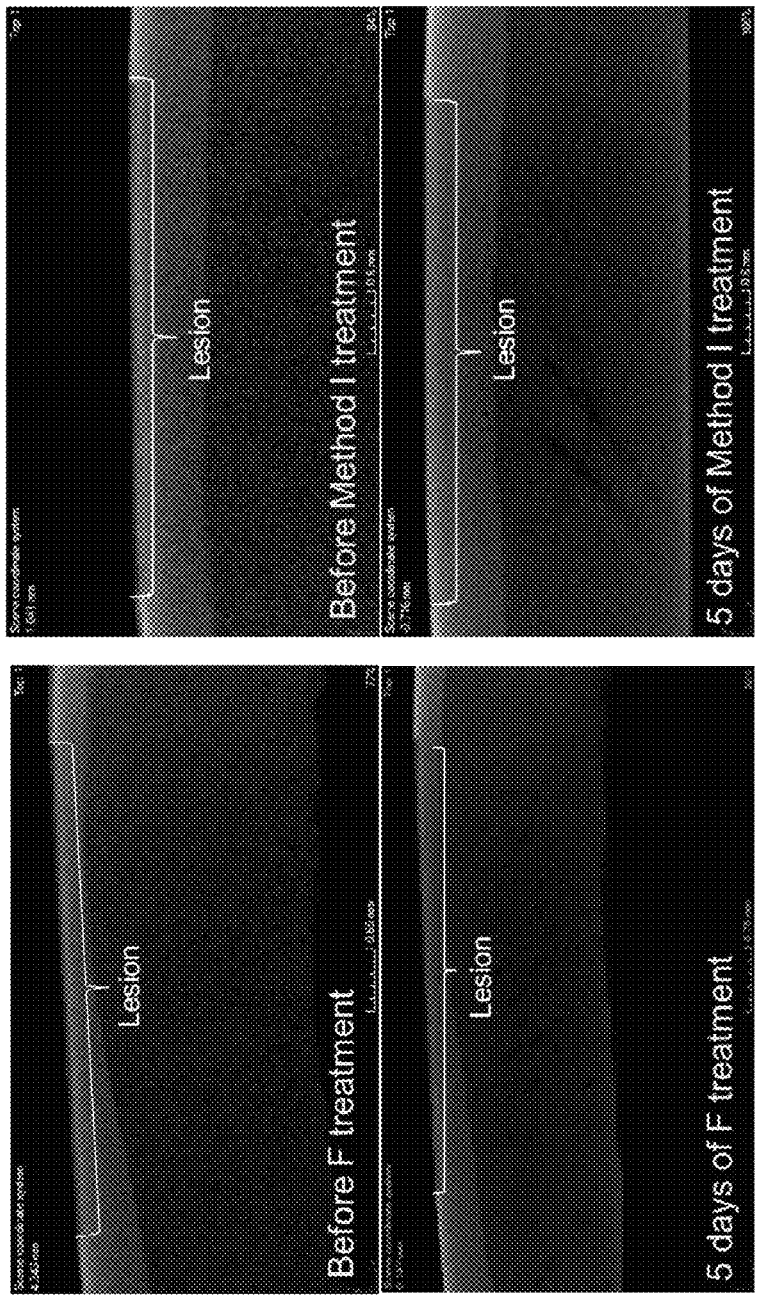
FIGS. 5-11 relate to various experiments performed on bovine teeth to evaluate aspects of examples techniques of the disclosure.
Figure 6:
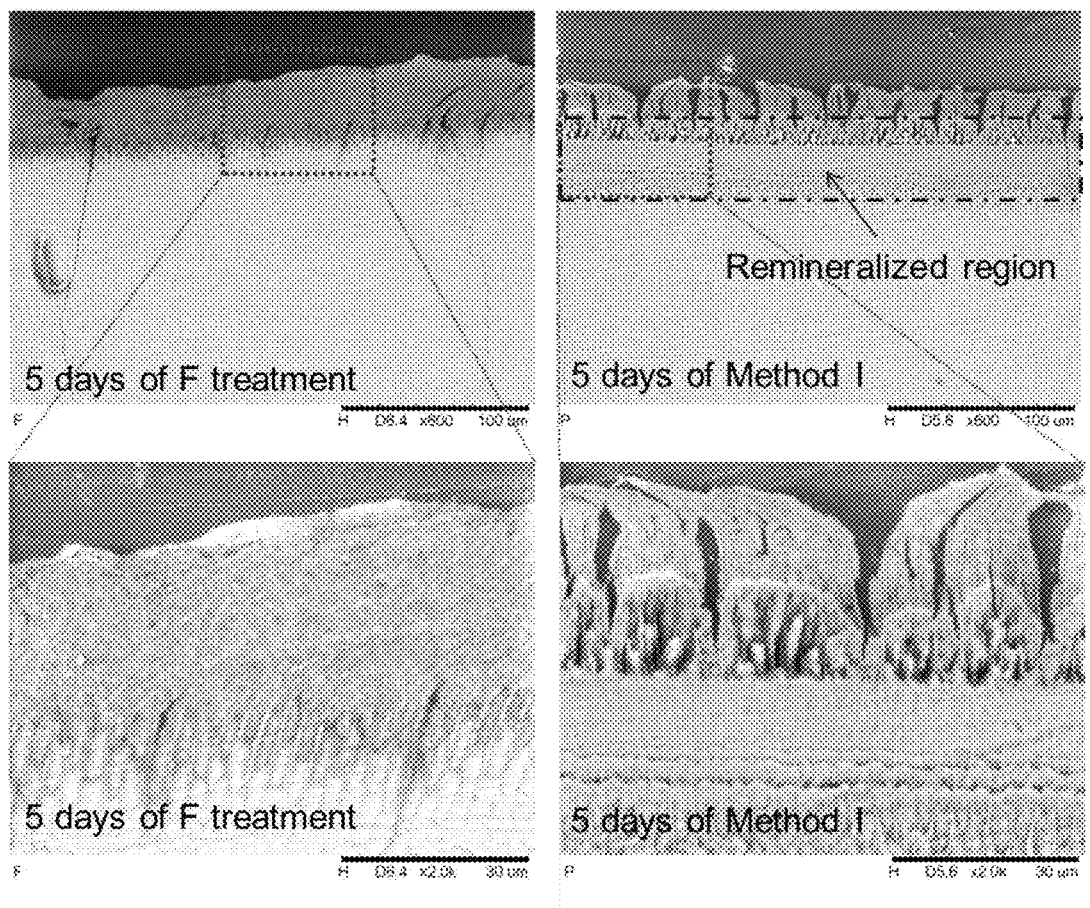

Example techniques of the present disclosure may be better than the aforementioned techniques for one or more of the following reasons: 1) example techniques of the disclosure may use a supersaturated calcium phosphate solution which is stabilized by polyanionic additives. In order to avoid the interference of saliva, this biomimetic mineralization solution, e.g., in the form of solution or gel, may be placed into a container/tray, such as modified braces. Then the braces will be placed on the patient for enamel restoration. Without the interference of saliva, the biomimetic mineralization solution may provide supersaturated liquid-like ACP which can quickly remineralize enamel lesions, e.g., as shown in FIGS. 5 and 6 described below. As described below, in an experiment carried out to compare fluoride treatment versus biomimetic mineralization treatment of enamel, after 5 days of remineralization, no significant remineralization of enamel was found using fluoride treatment. In contrast, enamel lesions were highly regressed after 5 days of the biomimetic mineralization treatment. 2) By using elastin-like polypeptides in combination with the biomimetic mineralization process, the structure, composition and aesthetics appearance of enamel were completely restored from enamel lesions (e.g., as shown in FIGS. 7-10 below).

EXPERIMENTAL RESULTS

Example I—Bovine Teeth

A first series of experiments were carried out to evaluate examples of the present disclosure related to the use of a polymer-stabilized biomimetic mineralization process to restore enamel defects of a tooth through remineralization of the enamel. Example in which a polymer-stabilized biomimetic mineralization process was applied but not in combination with an ELP process may be referred to as "Method I." Examples in which an ELP composition was used in combination with a polymer-stabilized biomimetic mineralization process may be referred to as "Method II."

Example 1—Mineralization of Enamel Lesion with the Polymer-Stabilized Biomimetic Mineralization Process Preparation of a polymer-stabilized biomimetic mineralization solution: Tri-buffered saline (TBS, pH7.4 at 37° C.) was prepared by mixing 5.72 g of Trizma HCl, 1.66 g of Trizma Base and 9 g of NaCl in one liter of distilled water. Calcium (9 mM $CaCl_2$) and phosphate (4.2 mM $K_2HPO_4$) solutions were made in TBS. Poly-L-aspartic acid sodium salt (Mw: 27,000 Da) was used as the biomimetic mineralization process-directing agent. It was dissolved in the aforementioned calcium solution at a concentration of 100-µg/mL before mixing an equal volume of the phosphate counterion solution.

A biomimetic mineralization solution was compounded as indicated in Table 2:

TABLE 2

Composition of the biomimetic mineralization solution

| Substances | Weight [g] | Concentration in final solution [mg/g] |
|---|---|---|
| Calcium chloride dihydrate | 0.658 | 0.65 |
| Potassium phosphate dibasic trihydrate | 0.483 | 0.47 |
| Tris[hydroxymethyl]aminomethane | 5.72 | 5.62 |
| Tris[hydroxymethyl]aminomethane hydrochloride | 1.66 | 1.63 |
| Sodium chloride | 9 | 8.84 |
| Sodium polyaspartate | 0.05 | 0.05 |
| Distilled water | 1000 | 982.73 |

FIG. 5 shows micro-CT images of bovine teeth specimens before and after fluoride (F) (images on the left) and the remineralization treatment using Method I (images on the right). The labelled enamel lesions are shown as dark bands which were darker than the non-demineralized region. After 5 days of F treatment, no density change was found on the dark band. In contrast, the dark band turned bright after 5 days of Method I treatment indicating the occurrence of remineralization. Artificial enamel lesions were created by incubating the teeth slices that were covered with nail varnish except a 3×3 mm window on buccal surfaces, in a lactic acid solution at 37° C. for 24 hours. In the fluoride treatment, a fluoride varnish containing 5% of NaF (DuraShield, Sultan Health Care) was applied on enamel lesion using a brush. The specimens were then stored in 30 ml of remineralization solution (1.5 mM/L calcium, 0.9 mM/L phosphate, 150 mM/L KCl, and 20 mM/L cacodylate buffer, pH7.0) at 37° C. for 5 days. In the Method I treatment, the specimens after 24 hours of demineralization were incubated in a biomimetic mineralization solution (4.5 mM/L calcium, 2.1 mM/L phosphate, and 50 µg/mL polyaspartate in Tris Buffer Saline pH7.4 at 37° C.). The remineralization solution was refreshed every 3 days.

FIG. 6 shows cross-sectional SEM images of enamel specimens after 5 days of F treatment (images on the left) or remineralization using Method I (images on the right). As shown, there was no sign of remineralization after fluoride treatment showing enamel lesion around 50 µm in depth. After Method I treatment, the biomimetic mineralization composition infiltrated into the enamel lesion and crystalized, making it brighter than the top un-remineralized region.

Example 2—Remineralization of Enamel Lesions with the Biomimetic Mineralization Process in Combination of the ELP Infiltration Preparation of ELP solutions: Lyophilized elastin-like polypeptides (HSS3) were added into distilled water at the concentration of 50 mg/mL and stored at 4° C. to be fully dissolved.

A ELP solution was compounded as follows:

TABLE 3

Table 3 shows the composition of the ELP solution

| Substance | Weight [g] | Concentration in final solution [mg/g] |
|---|---|---|
| HSS3 | 0.05 | 47.6 |
| Distilled water | 1 | 952.4 |

In Method II, polished bovine enamel was demineralized in a lactic acid at pH 4.5 for 48 hours to produce artificial lesions. The ELP solution was applied with a brush on air-dried enamel lesions and allowed to penetrate into the lesions for 5 min. Glutaraldehyde aqueous solution with concentration of 4 wt % was applied for 1 min to cross-link the ELPs. After carefully rinsing with distilled water, the bovine enamel specimens were incubated in the biomimetic mineralization solution for up to 10 days for enamel restoration.

Figure 7:
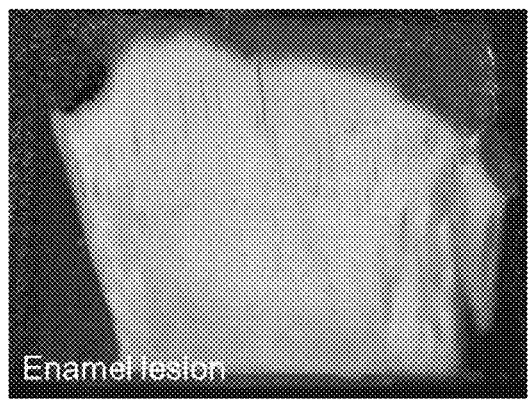
Figure 7:
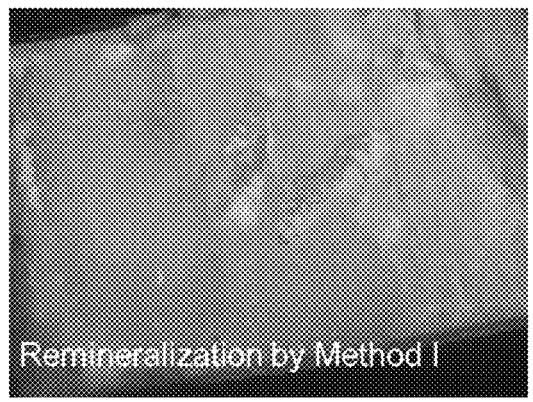
Figure 7:
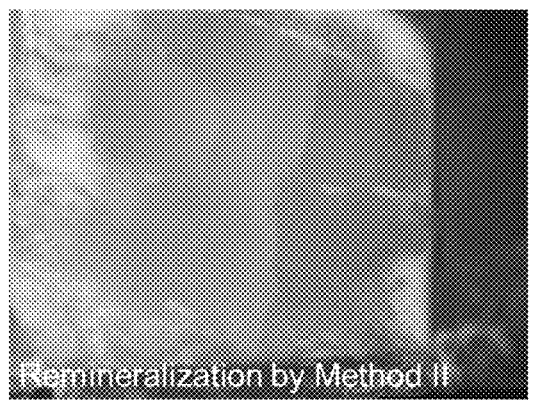

FIG. 7 shows images of an artificial enamel lesion generated by demineralization at pH4.5 for 48 hr (left), remineralized enamel lesion after 10 days of the biomimetic mineralization treatment (Method I, upper right) and remineralized enamel lesion after application of a layer of elastin-like polypeptides followed by 10 days of the biomimetic mineralization treatment (Method II, lower right). The enamel lesion appeared white. It regressed after 10 days of the biomimetic mineralization process as the white lesion turned transparent. After remineralization using Method II, the enamel lesion appeared translucent similar to the real aesthetic appearance of intact enamel.

Figure 8:
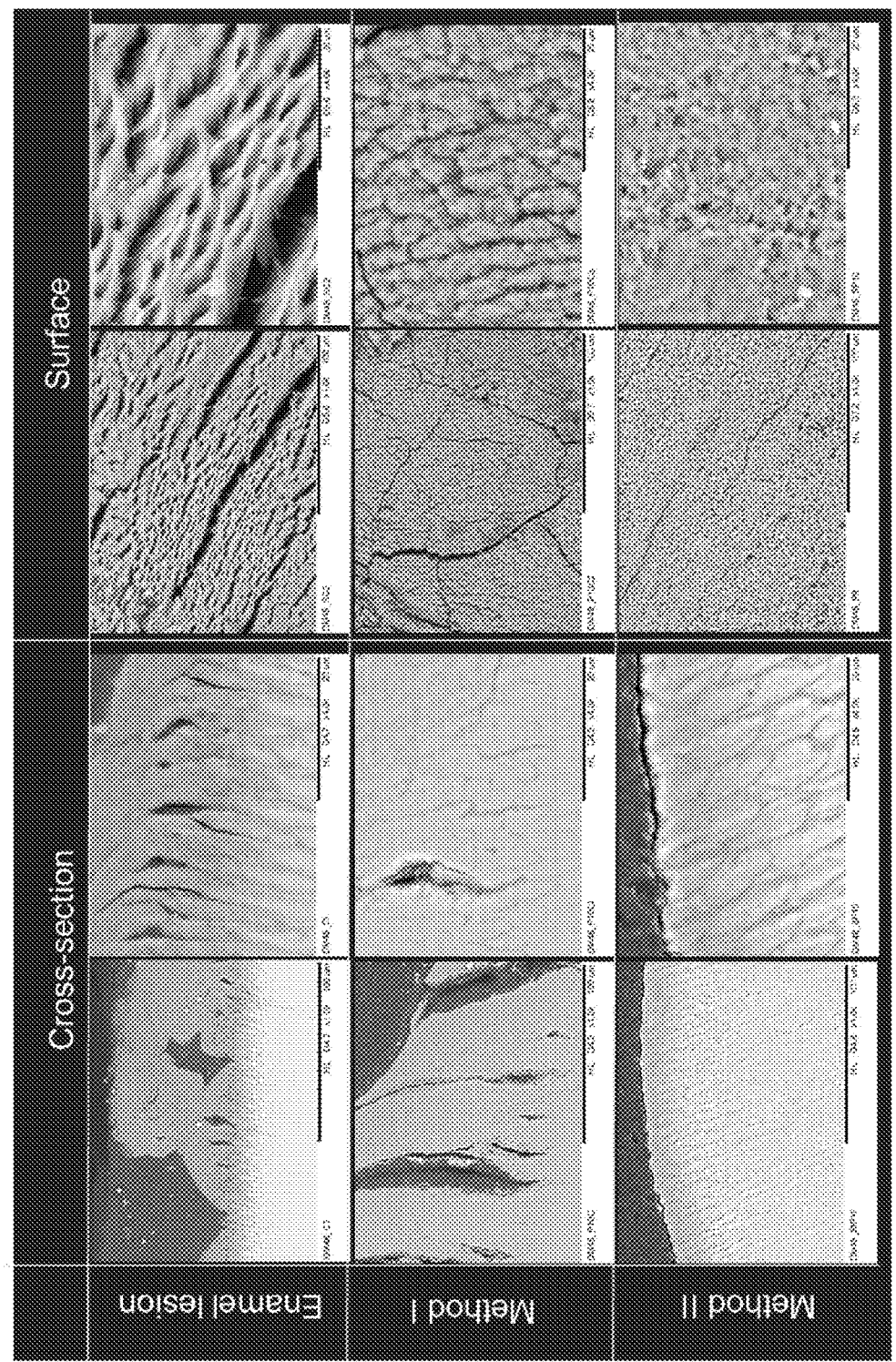

FIG. 8 shows SEM images of cross-sectional and surface view of an enamel lesion (top row), after 10 days of remineralization using Method I (middle row), and after 10 days of remineralization using Method II (bottom row). The artificial enamel lesion appeared as a dark band and the enamel rods were highly eroded, leaving a porous structure. After 10 days of remineralization by Method I, enamel rods were highly recovered at the enamel lesion. After treatment of Method II, the structure of enamel, rods and prismatic, were completely restored.

Figure 9:
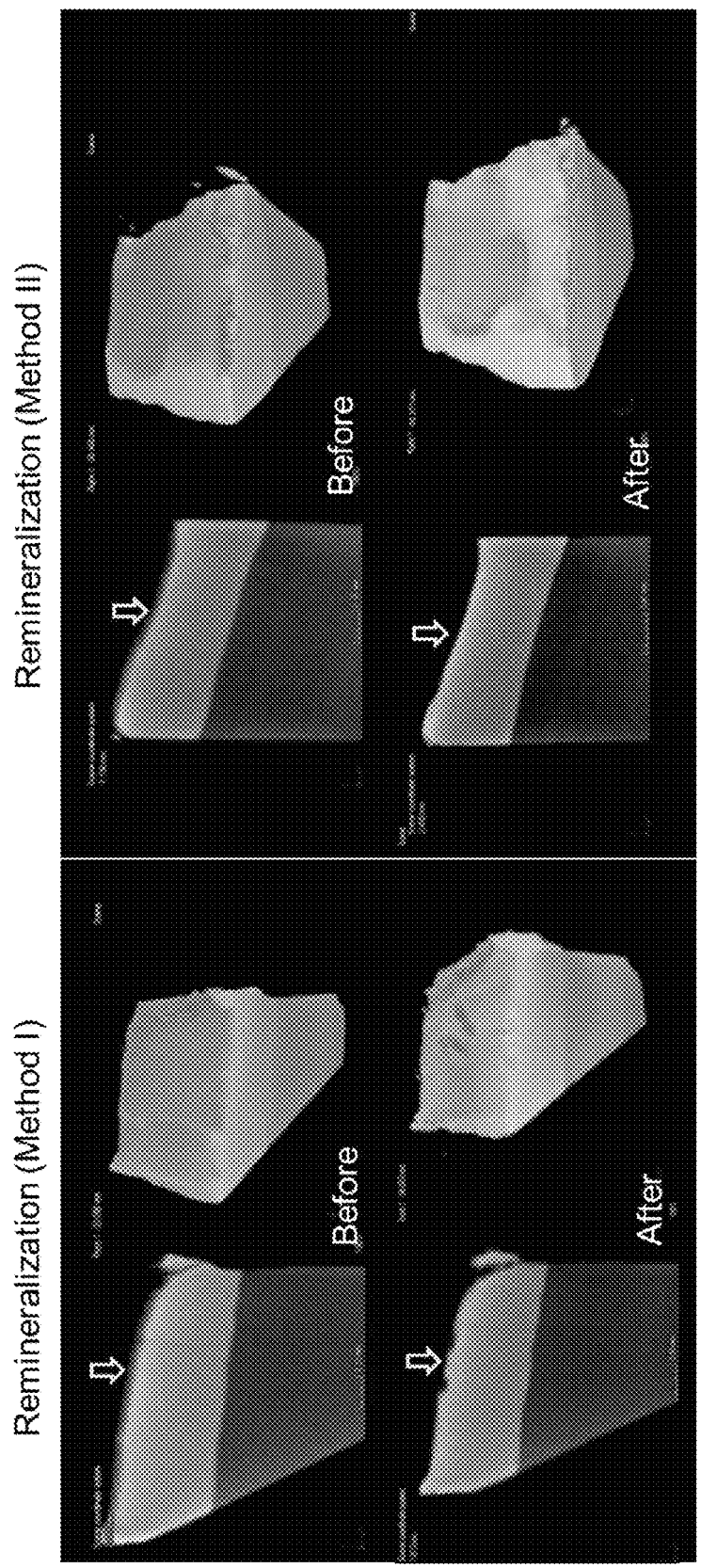

FIG. 9 shows microCT images of enamel lesions before and after remineralization treatment using Method I (images on left) and Method II for 10 days (images on right). As shown, the mineral density was highly increased after remineralization as the dark band (lesion) turned to bright. Also, big gaps of the lesion were restored using Method II.

Figure 10:
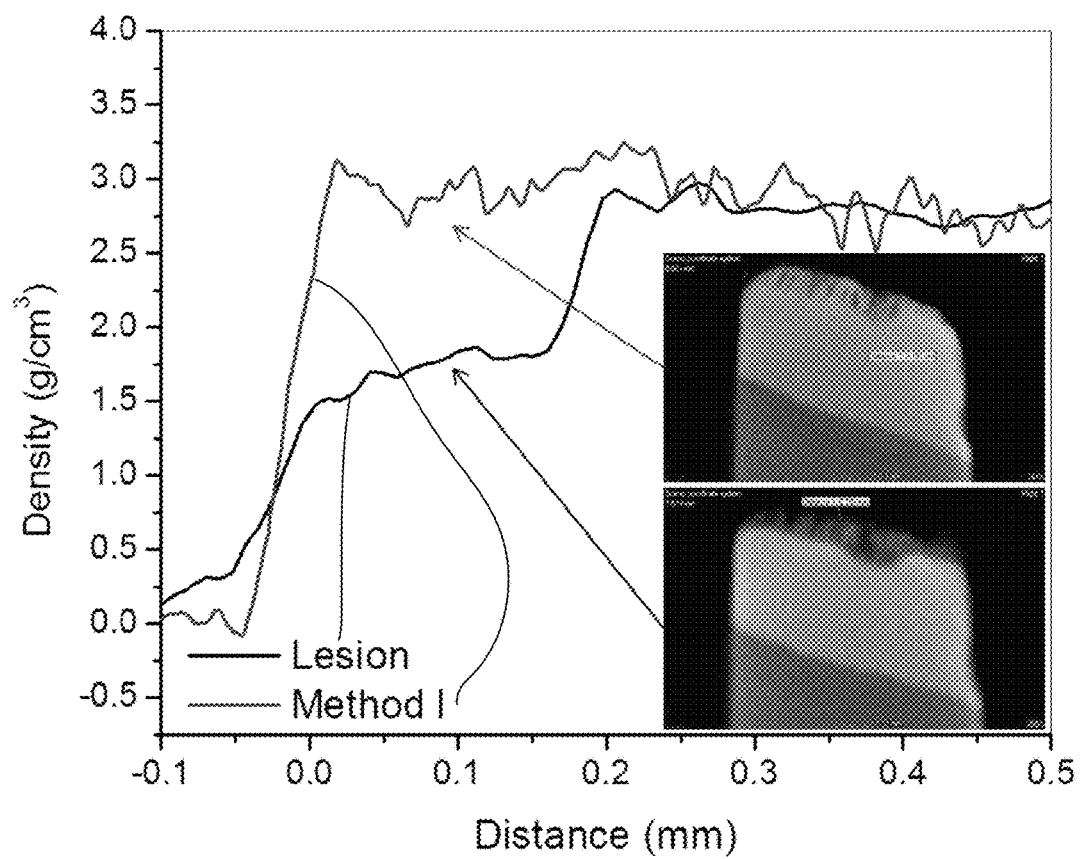

FIG. 10 is a plot of mineral density profiles of enamel lesion before and after 10 days of remineralization via Method I. The mineral density approached to the same level as that of intact enamel after remineralization.

Figure 11:
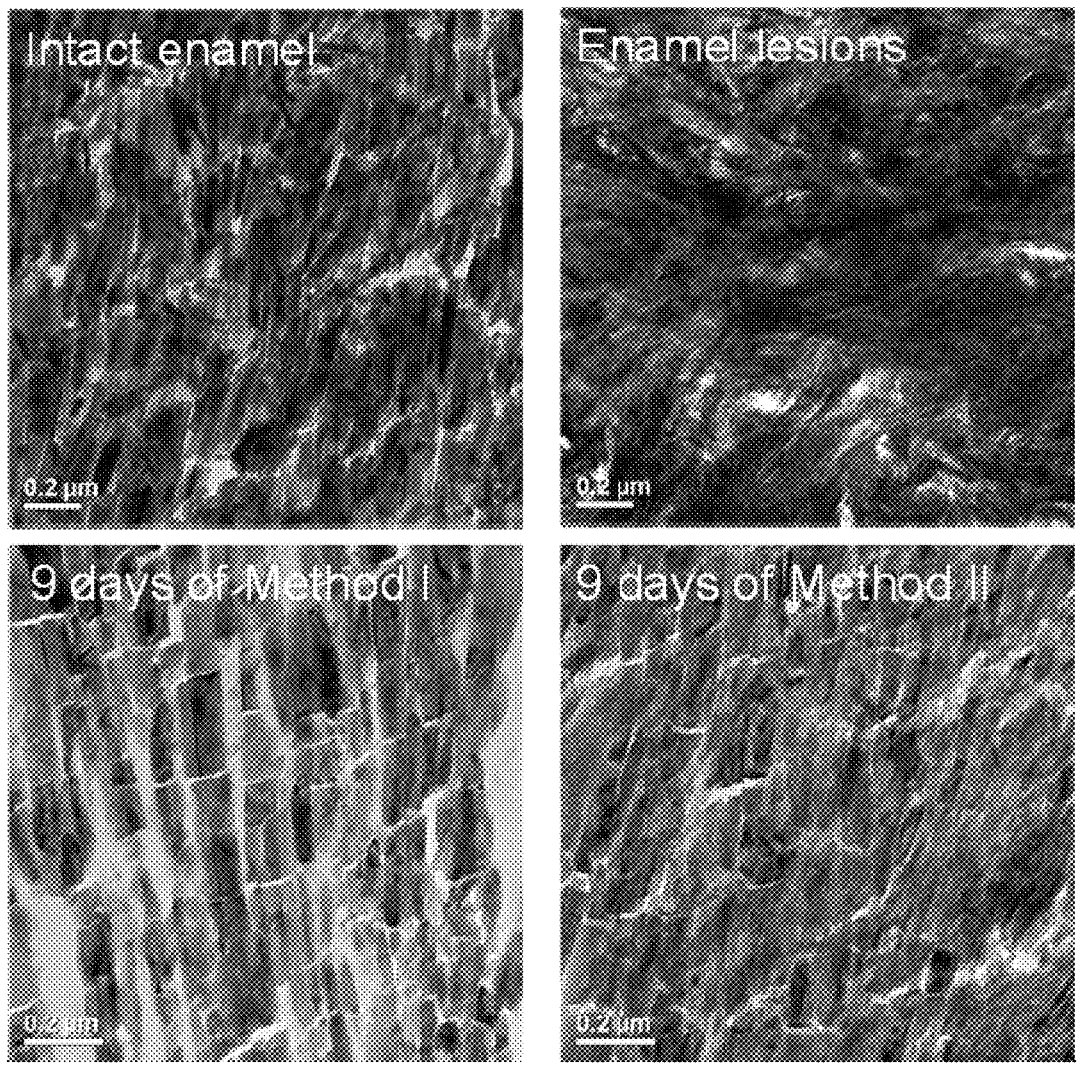

FIG. 11 are TEM images of enamel crystallites from intact enamel, artificial enamel lesion produced by incubating in a lactate buffer at pH4.5 for 48 hr, remineralized enamel using Method I and Method II. The intact enamel crystallites are 50-100 nm wide. They are partially dissolved by acid and are need-like in artificial lesion. Biomimetic remineralization using Method I regrow the partially dissolved needle-like enamel crystallites into large size. In the Method II treatment, the ELPs were infiltrated into the voids of enamel lesion and mineralized in a way to fully fill the voids of the enamel.

With experiments that have been carried out, it has been shown that, in some examples, 1) hydroxyapatite crystals deposit into demineralized enamel to produce net mineral gain; 2) hydroxyapatite crystals deposit into demineralized enamel to produce organized arrays of the crystals that grew along the c-axis of enamel rods; 3) hydroxyapatite crystals deposit in demineralized enamel to produce enamel rods, forming bundles of aligned hydroxyapatite crystallites; and 4) the structure, composition and aesthetic appearance of enamel may be restored from enamel lesion by applying a biomimetic mineralization process alone or in combination with application of ELPs.

Example II—Human Teeth

A second series of experiments were carried out to evaluate examples of the present disclosure related to the use of a polymer-stabilized biomimetic mineralization process to restore enamel defects of a tooth through remineralization of the enamel. The second series of experiments were carried out using human teeth rather than bovine teeth as in EXAMPLE I described above.

Figure 12:
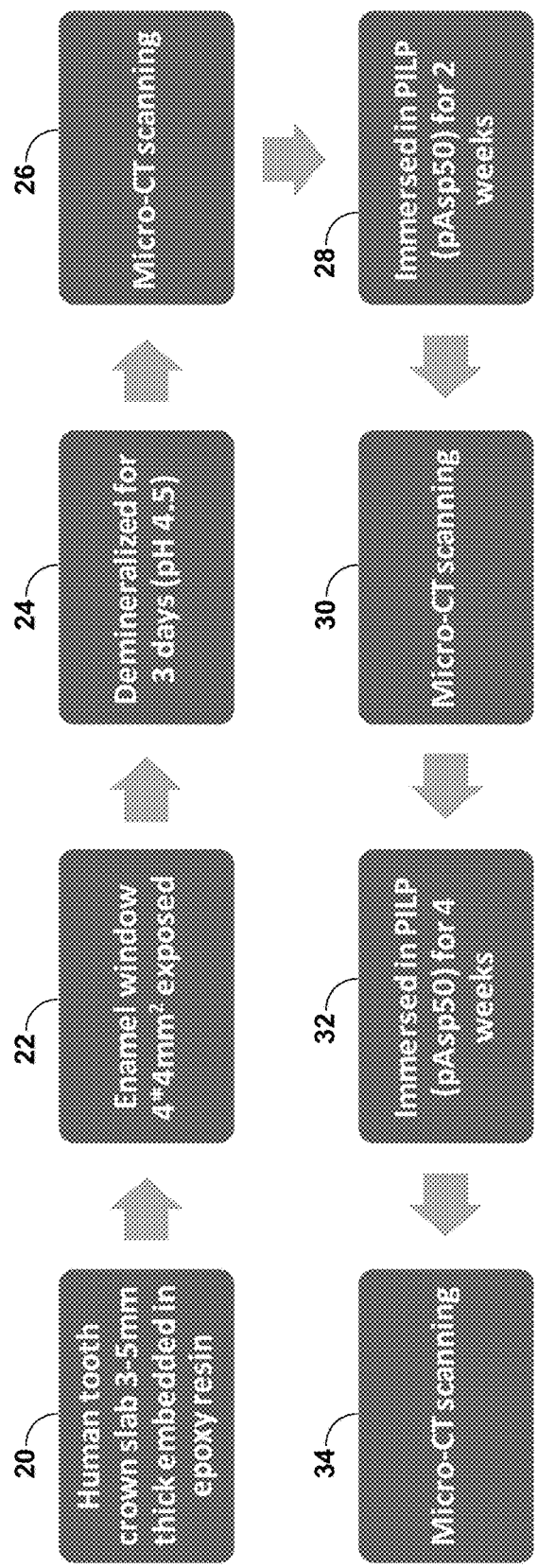
FIGS. 12-18B relate to various experiments performed on human teeth to evaluate aspects of examples techniques of the disclosure.

FIG. 12 is a flow diagram illustrating the experimental process used in the second series of experiments. As shown in FIG. 12, a human tooth crown slab about 3 millimeters (mm) to about 5 mm thick was embedded in epoxy resin (20). A window of enamel of about 4 mm by about 4 mm (approximately 16 square mm) was exposed by protecting the non-exposed area with nail varnish (22). The specimen was then demineralized for approximately three days in a demineralization solution at 37° C. (24). The demineralization solution had a pH of approximately 4.5 and had the composition indicated in Table 4. As a result of the treatment, hydroxyapatite crystals of the superficial layers of the exposed enamel were dissolved by the action of the acidic demineralization solution.

TABLE 4

| Demineralization solution | |
|---|---|
| Ions | Concentration (millimolar (mM)) |
| $Ca^{2+}$ | 2.0 |
| $HPO_4^{2-}$ | 2.0 |
| $Acetate^-$ | 75.0 |

Following the demineralization of the specimen (24), micro-CT scanning was performed (26) using a Micro-CT machine (XT H 225, Nikon Metrology Inc., Brighton, Mich., USA). The scanning was performed with a spatial resolution of 6.3 µm. Projection images were collected at 95 kV and 90 µA using 360 degrees of rotation, 708 ms of exposure, 720 projections and 4 frames per projection.

Following the micro-CT scanning (26), the specimen was immersed in a biomimetic mineralization solution (pASp50) containing 50 µg/ml poly-L-aspartic acid (Mw=27 kDa) with equal volumes of 9.0 mM $CaCl_2.2H_2O$ and 4.2 mM $K_2HPO_4$ solutions for two weeks (28), and then removed, dried in air overnight and scanned with a micro-CT scanner as performed before being immersed (30). Following the second round of micro-CT scanning, the specimen was immersed in the same pASp50 biomimetic mineralization solution for two additional weeks, to give a total immersion period of four weeks (32), and then removed and dried in air overnight before a third round of micro-CT scanning as performed previously (34).

Figures 13A, 13B, 13C:
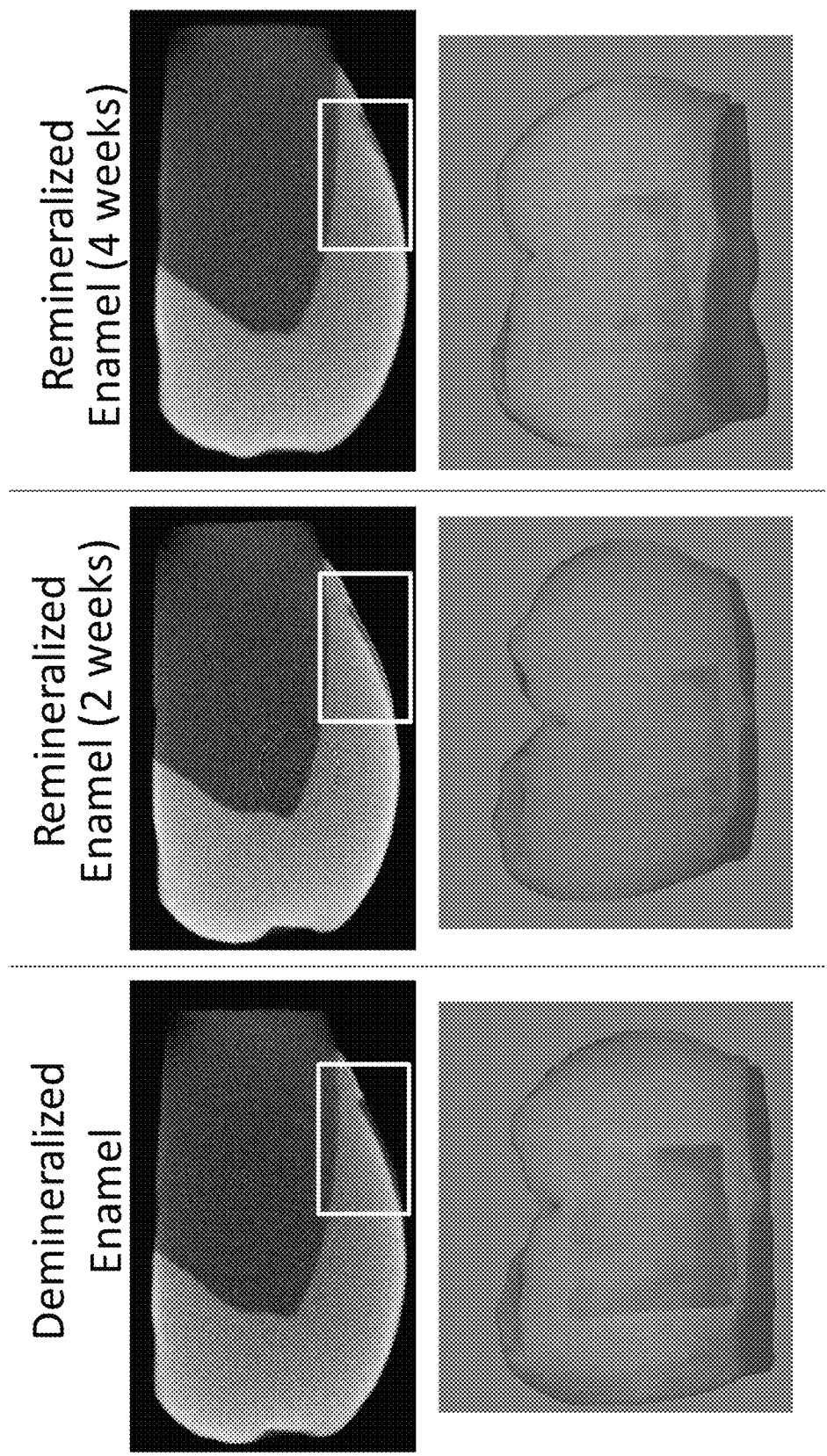

FIGS. 13A-13C are micro-CT images of the specimen following demineralization (24), following remineralization in the biomimetic mineralization solution for two weeks (28), and following remineralization in the biomimetic mineralization solution for four weeks, respectively, from a selected cross section (top image for each) including the demineralized enamel area (white box) and front view of the whole demineralized square area of the 3D reconstruction of the scanned tooth (bottom image for each). As shown, the demineralized area was partially remineralized after 2 weeks of immersion in the biomimetic mineralization solution pASp50. No further significant remineralization could be seen after 2 more weeks in the pASp50 solution.

Figure 14A:
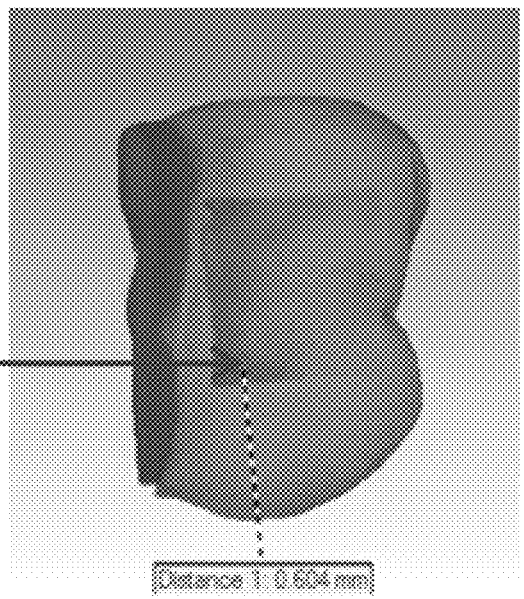
Figure 14B:
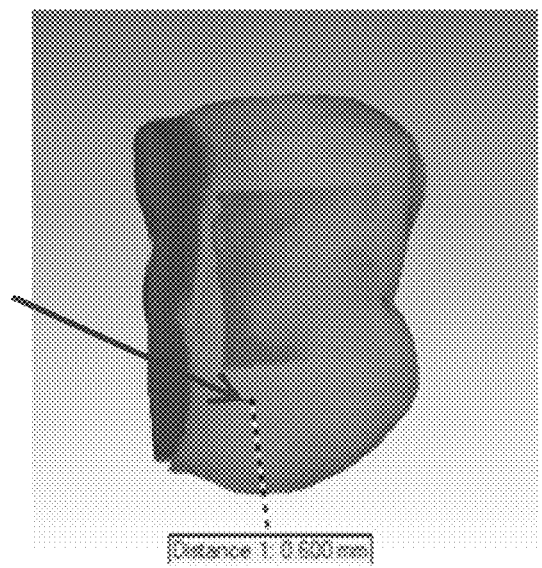

FIGS. 14A and 14B show the sampling points from the demineralized/remineralized region and protected sound-enamel region, respectively, where the through-depth mineral content was assessed and compared.

Figure 15:
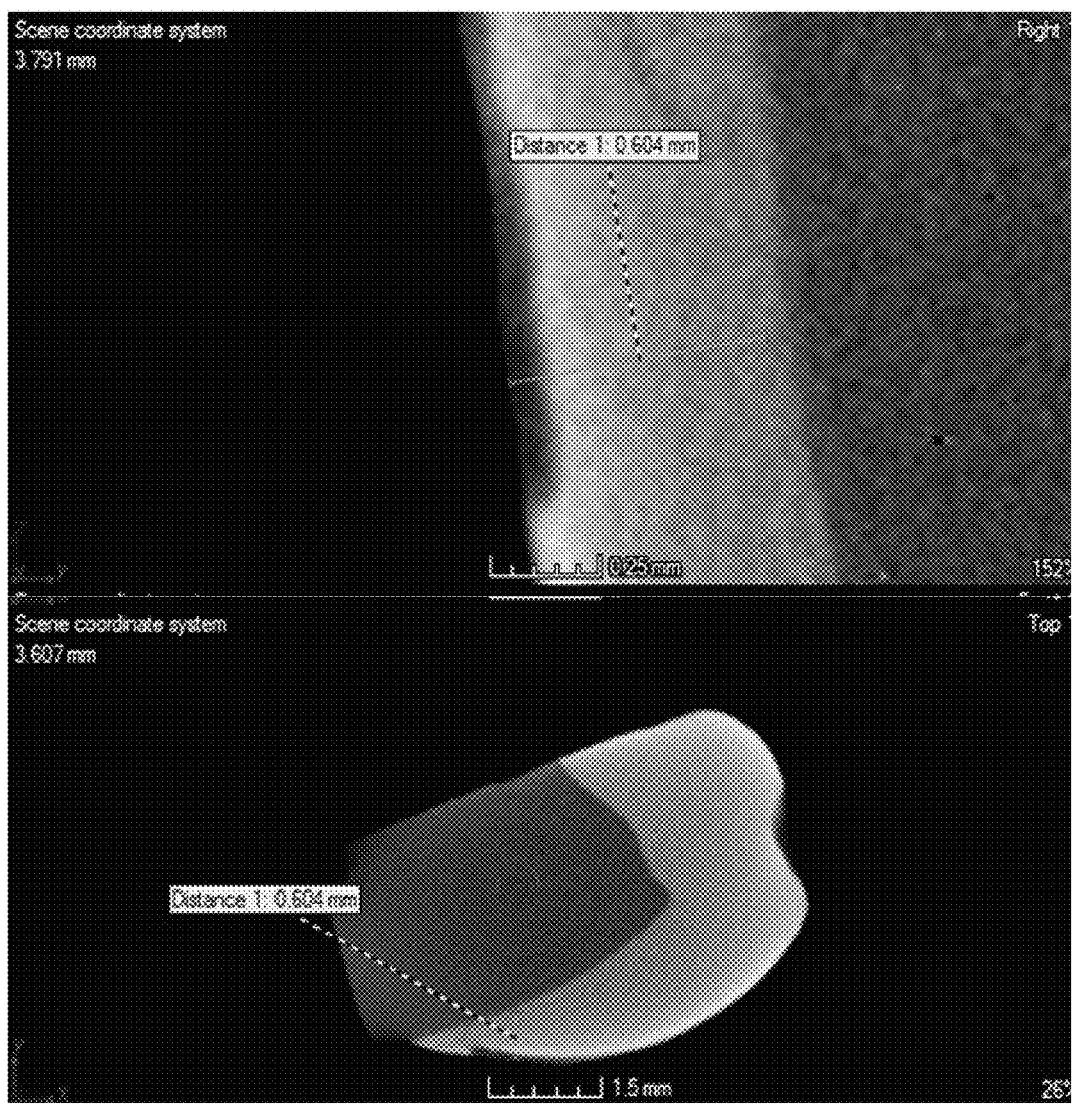

FIG. 15 shows the path on the selected cross section from the micro-CT images along which the through-depth mineral content of enamel was assessed at different time points. Relative mineral density in terms of volume percentage (vol %) was assumed to be proportional to the grey value, and sound enamel at a depth of 0.3 to 0.4 mm below surface was assumed to have a mineral content of 87 vol %.

Figure 16B:
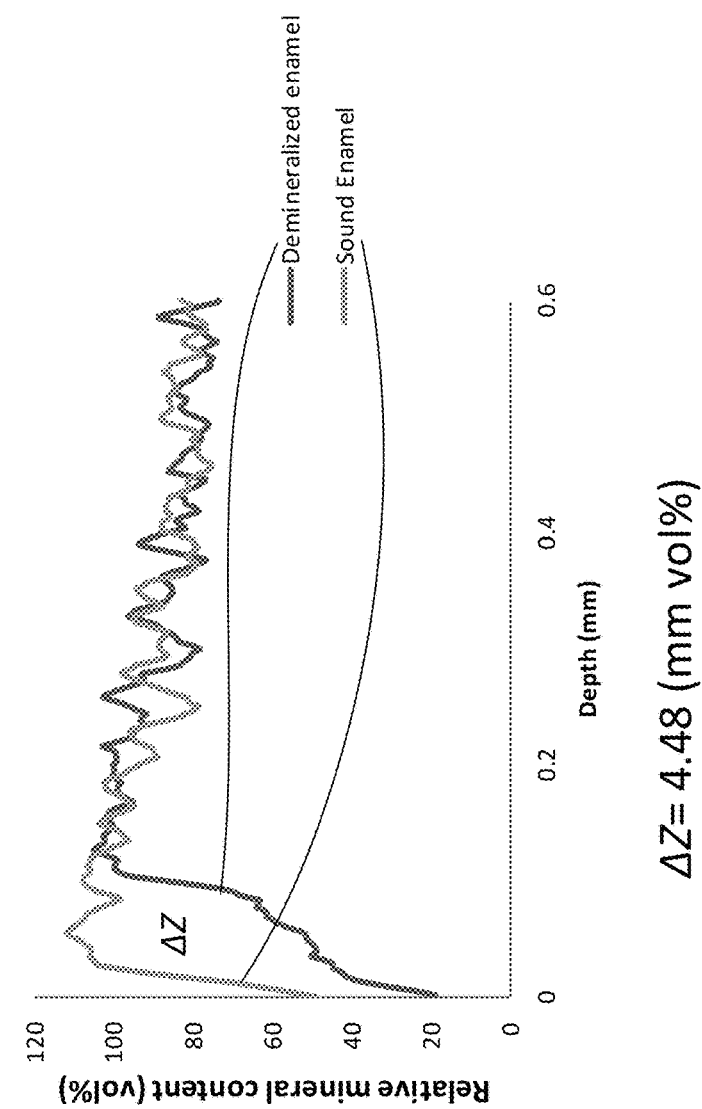
Figure 16A:
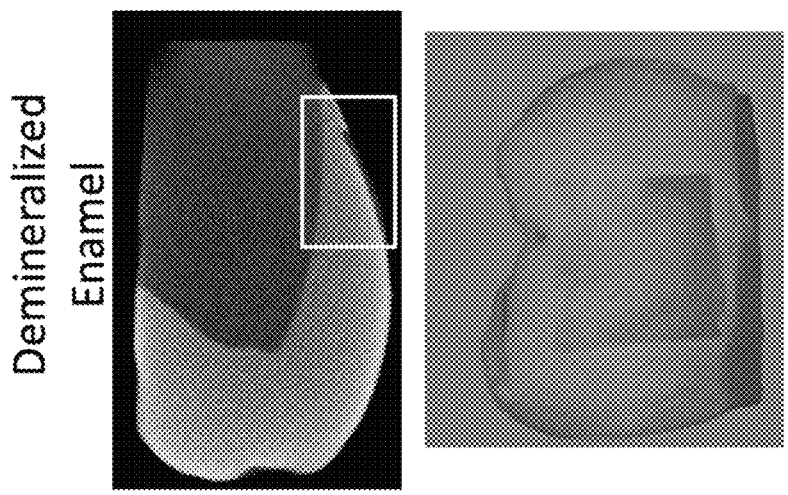

FIG. 16A is micro-CT images of the specimen following demineralization (24) but before remineralization (26). FIG. 16B is a plot of relative mineral content (volume percent) versus depth (mm) for the affected enamel following demineralization (24) but before remineralization (26) as well as for sound enamel. The integrated mineral loss (ΔZ) parameter refers to the cumulative mineral loss from the surface of the partially demineralized enamel to 0.6 mm under the enamel surface. As shown in FIG. 16B, the integrated mineral loss parameter was 4.48 (mm vol %).

Figure 17B:
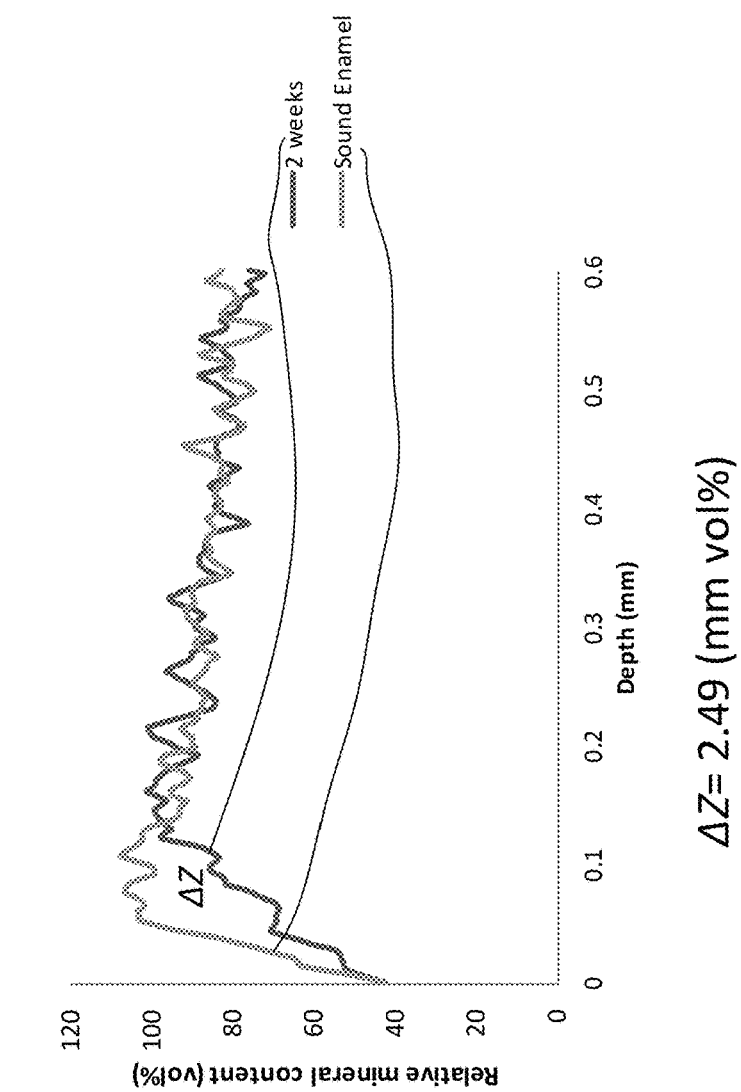
Figure 17A:
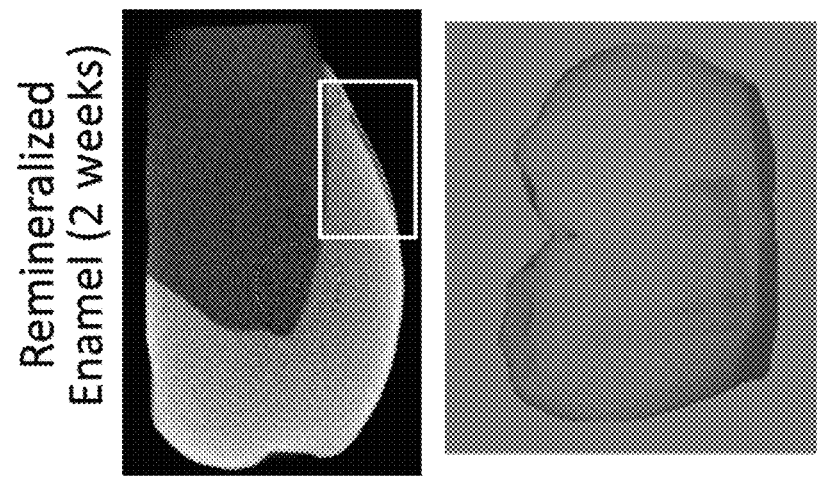

FIG. 17A is micro-CT images of the specimen following remineralization for two weeks (26) in the biomimetic mineralization solution. FIG. 17B is a plot of relative mineral content (volume percent) versus depth (mm) for the affected enamel following remineralization for two weeks (26) in the biomimetic mineralization solution as well as for sound enamel. The integrated mineral loss parameter was 2.49 (mm vol %). This result shows that the use of the pASp50 biomimetic mineralization solution for two weeks recovered almost half of the mineral content lost through demineralization.

Figure 18B:
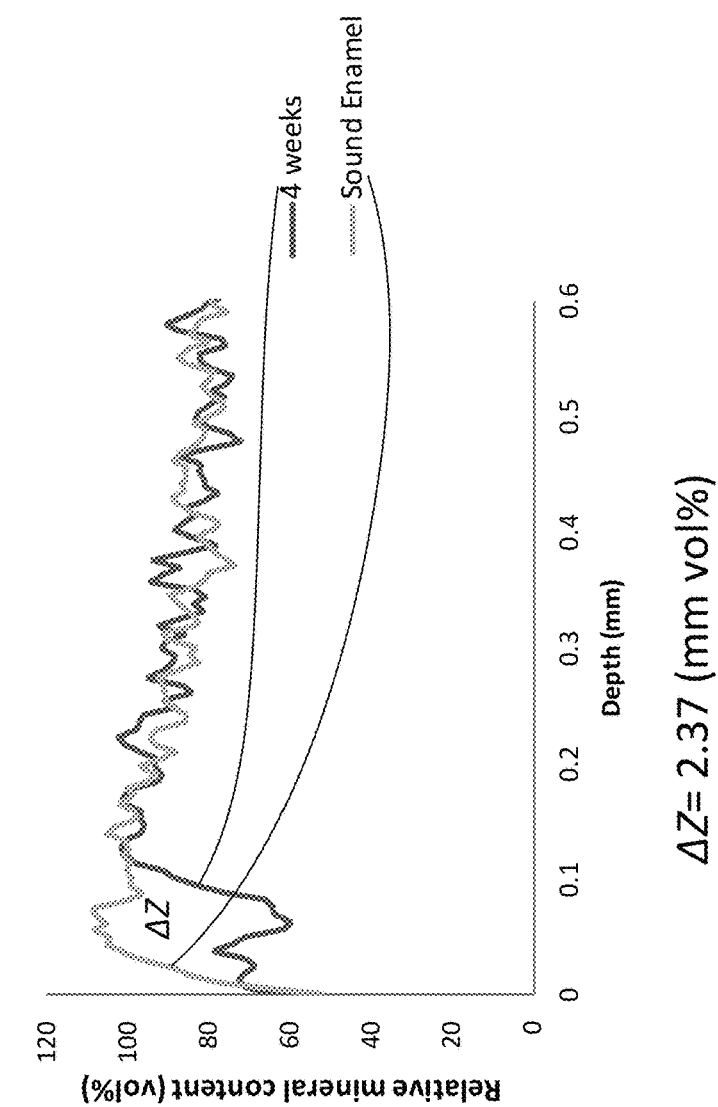
Figure 18A:
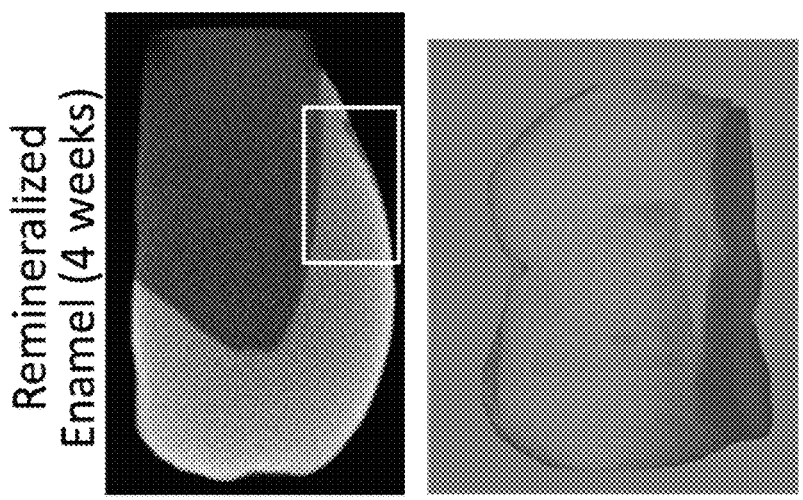

FIG. 18A is micro-CT images of the specimen following remineralization for an additional four weeks (28) in the biomimetic mineralization solution. FIG. 18B is a plot of relative mineral content (volume percent) versus depth (mm) for the affected enamel following remineralization for an additional four weeks (28) in the biomimetic mineralization solution as well as for sound enamel. The integrated mineral loss parameter was 2.37 (mm vol %). This result shows that the use of the pASp50 biomimetic mineralization solution for two more weeks did not recover additional significant amount of mineral than that recovered after 2 weeks in the pASp solution.

Various examples have been described. These and other examples are within the scope of the claims of this disclosure. In some examples, the disclosure relates to one or more of the following clauses:

Clause 1. A method comprising applying a biomimetic mineralization process to an enamel defect of a tooth, wherein the applied biomimetic mineralization process remineralizes the enamel defect.

Clause 2. The method of clause 1, wherein applying the biomimetic mineralization process to the enamel defect of the tooth comprises applying a biomimetic mineralization composition in an area of the enamel defect, wherein the biomimetic mineralization composition infiltrates into a porosity of the enamel defect and crystalizes to remineralize the enamel defect.

Clause 3. The method of clause 2, wherein the biomimetic mineralization composition includes a polyanionic additive, calcium, and phosphate.

Clause 4. The method of clause 3, wherein the polyanionic additive comprises at least one of polyaspartate, polyacrylic acid, or polyvinyl phosphonate.

Clause 5. The method of clause 3, wherein the polyanionic additive is configured to stabilize calcium phosphate within the composition to form a polymer stabilized amorphous calcium phosphate phase on the enamel, and wherein the liquid-like amorphous calcium phosphate phase adsorbs on partially dissolved hydroxyapatite nanocrystals and then crystalizes in a way to remineralize the enamel.

Clause 6. The method of clause 3, wherein the composition includes dipotassium phosphate, calcium chloride and polyaspartic acid.

Clause 7. The method of clause 2, wherein the biomimetic mineralization composition includes a biomimetic mineralization liquid solution or biomimetic mineralization gel.

Clause 8. The method of clause 2, wherein the biomimetic mineralization composition infiltrates into a porosity of the enamel defect and crystalizes to remineralize the enamel defect via capillary action.

Clause 9. The method of any of clauses 1 to 8, further comprising applying an elastin-like polypeptide (ELP) composition in the area of the enamel defect, wherein the applied ELP composition infiltrates into open pores of the enamel defect.

Clause 10. The method of clause 9, wherein applying the ELP composition on the surface of the tooth over the enamel defect comprises applying the ELP composition on the surface of the tooth over the enamel defect prior to the application of the biomimetic mineralization process.

Clause 11. The method of clause 9 or 10, wherein the ELP composition comprises at least one of elastin-like polypeptides with a size of about 5 to about 800 amino acids or a pentapeptide repeat sequence of VPGXG, where V is valine, P is proline, G is glycine, and X being isoleucine, valine or lysine.

Clause 12. The method of any of clauses 9-11, wherein the applied ELP composition forms an ELP matrix in the enamel defect via cross-linking of the ELP composition.

Clause 13. The method of any of clauses 9-12, wherein the biomimetic mineralization composition infiltrates into the ELP matrix and mineralizes in the ELP matrix.

Clause 14. The method of any of clause 9-13, wherein depositing the elastin-like polypeptide composition comprises an elastin-like recombinamer.

Clause 15. The method of any of clauses 1-14, wherein the enamel defect comprises an enamel deficient region in the enamel of the tooth caused by mineral loss.

Clause 16. The method of clause 15, wherein the enamel deficient region comprises at least one of voids, gaps, lesions, white spots, recesses or other discontinuities in the enamel.

Clause 17. The method of any of clauses 2-16, wherein the deposited biomimetic mineralization composition infiltrates into discontinuities in the enamel defect and mineralizes.

Clause 18. The method of clause 17, wherein the deposited biomimetic mineralization composition mineralizes by forming hydroxyapatite crystals.

Clause 19. A method comprising: applying an elastin-like polypeptide (ELP) composition in the area of the enamel defect, wherein the applied ELP composition infiltrates into open pores of the enamel defect; cross-linking the applied ELP composition to form matrices; and applying a biomimetic mineralization composition in the area of the enamel defect and matrices, wherein the biomimetic mineralization composition infiltrates into at least one of the porosity of the enamel defect or within the matrices, and crystalizes to remineralize the enamel defect.

Clause 20. The method of clause 19, wherein applying the ELP composition in the area of the enamel defect comprises applying the ELP composition prior to the application of the biomimetic mineralization composition.

Clause 21. The method of clause 19 or 20, wherein the ELP composition comprises at least one of elastin-like polypeptides with a size of about 5 to about 800 amino acids or a pentapeptide repeat sequence of VPGXG, where V is valine, P is proline, G is glycine, and X being isoleucine, valine or lysine.

Clause 22. The method of any of clauses 19-21, wherein the applied ELP composition forms an ELP matrix in the enamel defect via cross-linking of the ELP composition.

Clause 23. The method of any of clauses 19-21, wherein the biomimetic mineralization composition infiltrates into the ELP matrix and mineralizes in the ELP matrix.

Clause 24. The method of any of clause 19-23, wherein depositing the elastin-like polypeptide composition comprises an elastin-like recombinamer.

Clause 25. The method of any of clauses 19-24, wherein the biomimetic mineralization composition includes a polyanionic additive, calcium, and phosphate.

Clause 26. The method of clause 25, wherein the polyanionic additive comprises at least one of polyaspartate, polyacrylic acid, or polyvinyl phosphonate.

Clause 27. The method of clause 25, wherein the polyanionic additive is configured to stabilize calcium phosphate within the composition to form a polymer stabilized amorphous calcium phosphate phase on the enamel, and wherein the liquid-like amorphous calcium phosphate phase adsorbs on partially dissolved hydroxyapatite nanocrystals and then crystalizes in a way to remineralize the enamel.

Clause 28. The method of clause 25, wherein the composition includes dipotassium phosphate, calcium and polyaspartic acid.

Clause 29. The method of any of clauses 19-28, wherein the biomimetic mineralization composition includes a biomimetic mineralization liquid solution or biomimetic mineralization gel.

Clause 30. The method of any of clauses 19-29, wherein the biomimetic mineralization composition infiltrates into a porosity of the enamel defect and crystalizes to remineralize the enamel defect via capillary action.

Clause 31. The method of any of clauses 19-30, wherein the enamel defect comprises an enamel deficient region in the enamel of the tooth caused by mineral loss.

Clause 32. The method of clause 31, wherein the enamel deficient region comprises at least one of voids, gaps, lesions, white spots, recesses or other discontinuities in the enamel.

Clause 33. The method of any of clauses 19-32, wherein the deposited biomimetic mineralization composition infiltrates into discontinuities in the enamel defect and mineralizes.

Clause 34. The method of clause 33, wherein the deposited biomimetic mineralization composition mineralizes by forming hydroxyapatite crystals.

The invention claimed is:

1. A method comprising applying a biomimetic mineralization composition to an enamel defect of a tooth, wherein the biomimetic mineralization composition includes a polyanionic additive, calcium, and phosphate as active components, wherein the applied biomimetic mineralization composition remineralizes the enamel defect through direct crystallization of amorphous calcium phosphate into calcium phosphate minerals in the enamel defect.

2. The method of claim 1, wherein the biomimetic mineralization composition infiltrates into a porosity of the enamel defect and crystalizes to remineralize the enamel defect.

3. The method of claim 1, wherein the polyanionic additive comprises at least one of polyaspartate, polyacrylic acid, or polyvinyl phosphonate.

4. The method of claim 1, wherein the polyanionic additive is configured to stabilize calcium phosphate within the composition to form a polymer stabilized amorphous calcium phosphate phase on the enamel defect, and wherein the amorphous calcium phosphate phase adsorbs on partially dissolved hydroxyapatite nanocrystals and then crystalizes to remineralize the enamel defect.

5. The method of claim 1, wherein the biomimetic mineralization composition includes dipotassium phosphate, calcium chloride and polyaspartic acid.

6. The method of claim 1, wherein the biomimetic mineralization composition includes a biomimetic mineralization liquid solution or biomimetic mineralization gel.

7. The method of claim 2, wherein the biomimetic mineralization composition infiltrates into the porosity of the enamel defect and then crystalizes to remineralize the enamel defect via capillary action.

8. The method of claim 1, further comprising applying an elastin-like polypeptide (ELP) composition in an area of the enamel defect, wherein the applied ELP composition infiltrates into open pores of the enamel defect.

9. The method of claim 8, wherein applying the ELP composition in the area of the enamel defect comprises applying the ELP composition in the area of the enamel defect prior to the application of the biomimetic mineralization composition to the enamel defect.

10. The method of claim 9, wherein the ELP composition comprises at least one of elastin-like polypeptides with a size of about 5 to about 800 amino acids or a pentapeptide repeat sequence of VPGXG, where V is valine, P is proline, G is glycine, and X being isoleucine, valine or lysine.

11. The method of claim 8, wherein the ELP composition forms an ELP matrix in the enamel defect via cross-linking of the ELP composition.

12. The method of claim 11, wherein the biomimetic mineralization composition infiltrates into the ELP matrix and mineralizes in the ELP matrix.

13. The method of claim 8, wherein the ELP composition comprises an elastin-like recombinamer.

14. The method of claim 1, wherein the enamel defect comprises an enamel deficient region in the enamel of the tooth caused by mineral loss.

15. The method of claim 14, wherein the enamel deficient region comprises at least one of a void, a gap, a lesion, a white spot, or a recess in the enamel.

16. The method of claim 2, wherein the applied biomimetic mineralization composition infiltrates into discontinuities in the enamel defect and mineralizes.

17. The method of claim 16, wherein the applied biomimetic mineralization composition mineralizes by forming hydroxyapatite crystals.

18. A method comprising:
   applying an elastin-like polypeptide (ELP) composition in an area of an enamel defect, wherein the applied ELP composition infiltrates into open pores of the enamel defect;
   cross-linking the applied ELP composition to form matrices; and
   applying a biomimetic mineralization composition in the area of the enamel defect and matrices, wherein the applied biomimetic mineralization composition infiltrates into at least one of the porosity of the enamel defect or within the matrices, and crystalizes to remineralize the enamel defect through direct crystallization of amorphous calcium phosphate into calcium phosphate minerals in the enamel defect.

19. The method of claim 18, wherein applying the ELP composition in the area of the enamel defect comprises applying the ELP composition prior to the application of the biomimetic mineralization composition.

* * * * *

SEQUENCE LISTING

```
<160> NUMBER OF SEQ ID NOS: 5

<210> SEQ ID NO 1
<211> LENGTH: 607
<212> TYPE: PRT
<213> ORGANISM: Artificial Sequence
<220> FEATURE:
<223> OTHER INFORMATION: Synthetic peptide IK24

<400> SEQUENCE: 1

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
        35                  40                  45

Gly Ile Gly Val Pro Gly Ile Gly Val Pro Gly Ile Gly Val Pro Gly
    50                  55                  60

Ile Gly Val Pro Gly Lys Gly Val Pro Gly Ile Gly Val Pro Gly Ile
65                  70                  75                  80

Gly Val Pro Gly Ile Gly Val Pro Gly Ile Gly Val Pro Gly Lys Gly
                85                  90                  95

Val Pro Gly Ile Gly Val Pro Gly Ile Gly Val Pro Gly Ile Gly Val
            100                 105                 110

Pro Gly Ile Gly Val Pro Gly Lys Gly Val Pro Gly Ile Gly Val Pro
        115                 120                 125

Gly Ile Gly Val Pro Gly Ile Gly Val Pro Gly Ile Gly Val Pro Gly
    130                 135                 140

Lys Gly Val Pro Gly Ile Gly Val Pro Gly Ile Gly Val Pro Gly Ile
145                 150                 155                 160

Gly Val Pro Gly Ile Gly Val Pro Gly Lys Gly Val Pro Gly Ile Gly
                165                 170                 175

Val Pro Gly Ile Gly Val Pro Gly Ile Gly Val Pro Gly Ile Gly Val
            180                 185                 190

Pro Gly Lys Gly Val Pro Gly Ile Gly Val Pro Gly Ile Gly Val Pro
        195                 200                 205

Gly Ile Gly Val Pro Gly Ile Gly Val Pro Gly Lys Gly Val Pro Gly
    210                 215                 220

Ile Gly Val Pro Gly Ile Gly Val Pro Gly Ile Gly Val Pro Gly Ile
225                 230                 235                 240
```

Gly Val Pro Gly Lys Gly Val Pro Gly Ile Gly Val Pro Gly Ile Gly
                245                 250                 255

Val Pro Gly Ile Gly Val Pro Gly Ile Gly Val Pro Gly Lys Gly Val
            260                 265                 270

Pro Gly Ile Gly Val Pro Gly Ile Gly Val Pro Gly Ile Gly Val Pro
        275                 280                 285

Gly Ile Gly Val Pro Gly Lys Gly Val Pro Gly Ile Gly Val Pro Gly
    290                 295                 300

Ile Gly Val Pro Gly Ile Gly Val Pro Gly Ile Gly Val Pro Gly Lys
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Lys Gly Val Pro Gly Ile Gly Val
            340                 345                 350

Pro Gly Ile Gly Val Pro Gly Ile Gly Val Pro Gly Ile Gly Val Pro
        355                 360                 365

Gly Lys Gly Val Pro Gly Ile Gly Val Pro Gly Ile Gly Val Pro Gly
    370                 375                 380

Ile Gly Val Pro Gly Ile Gly Val Pro Gly Lys Gly Val Pro Gly Ile
385                 390                 395                 400

Gly Val Pro Gly Ile Gly Val Pro Gly Ile Gly Val Pro Gly Ile Gly
                405                 410                 415

Val Pro Gly Lys Gly Val Pro Gly Ile Gly Val Pro Gly Ile Gly Val
            420                 425                 430

Pro Gly Ile Gly Val Pro Gly Ile Gly Val Pro Gly Lys Gly Val Pro
        435                 440                 445

Gly Ile Gly Val Pro Gly Ile Gly Val Pro Gly Ile Gly Val Pro Gly
    450                 455                 460

Ile Gly Val Pro Gly Lys Gly Val Pro Gly Ile Gly Val Pro Gly Ile
465                 470                 475                 480

Gly Val Pro Gly Ile Gly Val Pro Gly Ile Gly Val Pro Gly Lys Gly
                485                 490                 495

Val Pro Gly Ile Gly Val Pro Gly Ile Gly Val Pro Gly Ile Gly Val
            500                 505                 510

Pro Gly Ile Gly Val Pro Gly Lys Gly Val Pro Gly Ile Gly Val Pro
        515                 520                 525

Gly Ile Gly Val Pro Gly Ile Gly Val Pro Gly Ile Gly Val Pro Gly
    530                 535                 540

Lys Gly Val Pro Gly Ile Gly Val Pro Gly Ile Gly Val Pro Gly Ile
545                 550                 555                 560

Gly Val Pro Gly Ile Gly Val Pro Gly Lys Gly Val Pro Gly Ile Gly
                565                 570                 575

Val Pro Gly Ile Gly Val Pro Gly Ile Gly Val Pro Gly Ile Gly Val
            580                 585                 590

Pro Gly Lys Gly Val Pro Gly Ile Gly Val Pro Gly Ile Gly Val
        595                 600                 605

<210> SEQ ID NO 2
<211> LENGTH: 607
<212> TYPE: PRT
<213> ORGANISM: Artificial Sequence
<220> FEATURE:
<223> OTHER INFORMATION: Synthetic peptide VK24

<400> SEQUENCE: 2

```
Met Glu Ser Leu Leu Pro Val Pro Gly Val Gly Val Pro Gly Val Gly
1               5                   10                  15
Val Pro Gly Lys Gly Val Pro Gly Val Gly Val Pro Gly Val Gly Val
                20                  25                  30
Pro Gly Val Gly Val Pro Gly Val Gly Val Pro Gly Lys Gly Val Pro
            35                  40                  45
Gly Val Gly Val Pro Gly Val Gly Val Pro Gly Val Gly Val Pro Gly
        50                  55                  60
Val Gly Val Pro Gly Lys Gly Val Pro Gly Val Gly Val Pro Gly Val
65                  70                  75                  80
Gly Val Pro Gly Val Gly Val Pro Gly Val Gly Val Pro Gly Lys Gly
                85                  90                  95
Val Pro Gly Val Gly Val Pro Gly Val Gly Val Pro Gly Val Gly Val
            100                 105                 110
Pro Gly Val Gly Val Pro Gly Lys Gly Val Pro Gly Val Gly Val Pro
        115                 120                 125
Gly Val Gly Val Pro Gly Val Gly Val Pro Gly Val Gly Val Pro Gly
    130                 135                 140
Lys Gly Val Pro Gly Val Gly Val Pro Gly Val Gly Val Pro Gly Val
145                 150                 155                 160
Gly Val Pro Gly Val Gly Val Pro Gly Lys Gly Val Pro Gly Val Gly
                165                 170                 175
Val Pro Gly Val Gly Val Pro Gly Val Gly Val Pro Gly Val Gly Val
            180                 185                 190
Pro Gly Lys Gly Val Pro Gly Val Gly Val Pro Gly Val Gly Val Pro
        195                 200                 205
Gly Val Gly Val Pro Gly Val Gly Val Pro Gly Lys Gly Val Pro Gly
    210                 215                 220
Val Gly Val Pro Gly Val Gly Val Pro Gly Val Gly Val Pro Gly Val
225                 230                 235                 240
Gly Val Pro Gly Lys Gly Val Pro Gly Val Gly Val Pro Gly Val Gly
                245                 250                 255
Val Pro Gly Val Gly Val Pro Gly Val Gly Val Pro Gly Lys Gly Val
            260                 265                 270
Pro Gly Val Gly Val Pro Gly Val Gly Val Pro Gly Val Gly Val Pro
        275                 280                 285
Gly Val Gly Val Pro Gly Lys Gly Val Pro Gly Val Gly Val Pro Gly
    290                 295                 300
Val Gly Val Pro Gly Val Gly Val Pro Gly Val Gly Val Pro Gly Lys
305                 310                 315                 320
Gly Val Pro Gly Val Gly Val Pro Gly Val Gly Val Pro Gly Val Gly
                325                 330                 335
Val Pro Gly Val Gly Val Pro Gly Lys Gly Val Pro Gly Val Gly Val
            340                 345                 350
Pro Gly Val Gly Val Pro Gly Val Gly Val Pro Gly Val Gly Val Pro
        355                 360                 365
Gly Lys Gly Val Pro Gly Val Gly Val Pro Gly Val Gly Val Pro Gly
    370                 375                 380
Val Gly Val Pro Gly Val Gly Val Pro Gly Lys Gly Val Pro Gly Val
385                 390                 395                 400
Gly Val Pro Gly Val Gly Val Pro Gly Val Gly Val Pro Gly Val Gly
                405                 410                 415
```

```
Val Pro Gly Lys Gly Val Pro Gly Val Pro Gly Val
            420             425             430

Pro Gly Val Gly Val Pro Gly Val Gly Val Pro Gly Lys Gly Val Pro
        435                 440                 445

Gly Val Gly Val Pro Gly Val Gly Val Pro Gly Val Gly Val Pro Gly
    450                 455                 460

Val Gly Val Pro Gly Lys Gly Val Pro Gly Val Gly Val Pro Gly Val
465                 470                 475                 480

Gly Val Pro Gly Val Gly Val Pro Gly Val Gly Val Pro Gly Lys Gly
                485                 490                 495

Val Pro Gly Val Gly Val Pro Gly Val Gly Val Pro Gly Val Gly Val
            500                 505                 510

Pro Gly Val Gly Val Pro Gly Lys Gly Val Pro Gly Val Gly Val Pro
        515                 520                 525

Gly Val Gly Val Pro Gly Val Gly Val Pro Gly Val Gly Val Pro Gly
    530                 535                 540

Lys Gly Val Pro Gly Val Gly Val Pro Gly Val Gly Val Pro Gly Val
545                 550                 555                 560

Gly Val Pro Gly Val Gly Val Pro Gly Lys Gly Val Pro Gly Val Gly
                565                 570                 575

Val Pro Gly Val Gly Val Pro Gly Val Gly Val Pro Gly Val Gly Val
            580                 585                 590

Pro Gly Lys Gly Val Pro Gly Val Gly Val Pro Gly Val Gly Val
        595                 600                 605

<210> SEQ ID NO 3
<211> LENGTH: 877
<212> TYPE: PRT
<213> ORGANISM: Artificial Sequence
<220> FEATURE:
<223> OTHER INFORMATION: Synthetic peptide REDV

<400> SEQUENCE: 3

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Glu
            20                  25                  30

Glu Ile Gln Ile Gly His Ile Pro Arg Glu Asp Val Asp Tyr His Leu
        35                  40                  45

Tyr Pro Val Pro Gly Ile Gly Val Pro Gly Ile Gly Val Pro Gly Lys
    50                  55                  60

Gly Val Pro Gly Ile Gly Val Pro Gly Ile Gly Val Gly Val Ala Pro
65                  70                  75                  80

Gly Val Gly Val Ala Pro Gly Val Gly Val Ala Pro Gly Val Pro Gly
                85                  90                  95

Ile Gly Val Pro Gly Ile Gly Val Pro Gly Lys Gly Val Pro Gly Ile
            100                 105                 110

Gly Val Pro Gly Ile Gly Glu Glu Ile Gln Ile Gly His Ile Pro Arg
        115                 120                 125

Glu Asp Val Asp Tyr His Leu Tyr Pro Val Pro Gly Ile Gly Val Pro
    130                 135                 140

Gly Ile Gly Val Pro Gly Lys Gly Val Pro Gly Ile Gly Val Pro Gly
145                 150                 155                 160

Ile Gly Val Gly Val Ala Pro Gly Val Gly Val Ala Pro Gly Val Gly
                165                 170                 175
```

-continued

Val Ala Pro Gly Val Pro Gly Ile Gly Val Pro Gly Ile Gly Val Pro
            180                 185                 190

Gly Lys Gly Val Pro Gly Ile Gly Val Pro Gly Ile Gly Glu Glu Ile
        195                 200                 205

Gln Ile Gly His Ile Pro Arg Glu Asp Val Asp Tyr His Leu Tyr Pro
    210                 215                 220

Val Pro Gly Ile Gly Val Pro Gly Ile Gly Val Pro Gly Lys Gly Val
225                 230                 235                 240

Pro Gly Ile Gly Val Pro Gly Ile Gly Val Gly Val Ala Pro Gly Val
            245                 250                 255

Gly Val Ala Pro Gly Val Gly Val Ala Pro Gly Val Pro Gly Ile Gly
            260                 265                 270

Val Pro Gly Ile Gly Val Pro Gly Lys Gly Val Pro Gly Ile Gly Val
        275                 280                 285

Pro Gly Ile Gly Glu Glu Ile Gln Ile Gly His Ile Pro Arg Glu Asp
        290                 295                 300

Val Asp Tyr His Leu Tyr Pro Val Pro Gly Ile Gly Val Pro Gly Ile
305                 310                 315                 320

Gly Val Pro Gly Lys Gly Val Pro Gly Ile Gly Val Pro Gly Ile Gly
            325                 330                 335

Val Gly Val Ala Pro Gly Val Gly Val Ala Pro Gly Val Gly Val Ala
            340                 345                 350

Pro Gly Val Pro Gly Ile Gly Val Pro Gly Ile Gly Val Pro Gly Lys
        355                 360                 365

Gly Val Pro Gly Ile Gly Val Pro Gly Ile Gly Glu Glu Ile Gln Ile
        370                 375                 380

Gly His Ile Pro Arg Glu Asp Val Asp Tyr His Leu Tyr Pro Val Pro
385                 390                 395                 400

Gly Ile Gly Val Pro Gly Ile Gly Val Pro Gly Lys Gly Val Pro Gly
            405                 410                 415

Ile Gly Val Pro Gly Ile Gly Val Gly Val Ala Pro Gly Val Gly Val
            420                 425                 430

Ala Pro Gly Val Gly Val Ala Pro Gly Val Pro Gly Ile Gly Val Pro
        435                 440                 445

Gly Ile Gly Val Pro Gly Lys Gly Val Pro Gly Ile Gly Val Pro Gly
    450                 455                 460

Ile Gly Glu Glu Ile Gln Ile Gly His Ile Pro Arg Glu Asp Val Asp
465                 470                 475                 480

Tyr His Leu Tyr Pro Val Pro Gly Ile Gly Val Pro Gly Ile Gly Val
            485                 490                 495

Pro Gly Lys Gly Val Pro Gly Ile Gly Val Pro Gly Ile Gly Val Gly
        500                 505                 510

Val Ala Pro Gly Val Gly Val Ala Pro Gly Val Gly Val Ala Pro Gly
        515                 520                 525

Val Pro Gly Ile Gly Val Pro Gly Ile Gly Val Pro Gly Lys Gly Val
        530                 535                 540

Pro Gly Ile Gly Val Pro Gly Ile Gly Glu Glu Ile Gln Ile Gly His
545                 550                 555                 560

Ile Pro Arg Glu Asp Val Asp Tyr His Leu Tyr Pro Val Pro Gly Ile
            565                 570                 575

Gly Val Pro Gly Ile Gly Val Pro Gly Lys Gly Val Pro Gly Ile Gly
            580                 585                 590

Val Pro Gly Ile Gly Val Gly Val Ala Pro Gly Val Gly Val Ala Pro

```
                    595                 600                 605
Gly Val Gly Val Ala Pro Gly Val Pro Gly Ile Gly Val Pro Gly Ile
            610                 615                 620
Gly Val Pro Gly Lys Gly Val Pro Gly Ile Gly Val Pro Gly Ile Gly
625                 630                 635                 640
Glu Glu Ile Gln Ile Gly His Ile Pro Arg Glu Asp Val Asp Tyr His
                645                 650                 655
Leu Tyr Pro Val Pro Gly Ile Gly Val Pro Gly Ile Gly Val Pro Gly
            660                 665                 670
Lys Gly Val Pro Gly Ile Gly Val Pro Gly Ile Gly Val Gly Val Ala
675                 680                 685
Pro Gly Val Gly Val Ala Pro Gly Val Gly Val Ala Pro Gly Val Pro
690                 695                 700
Gly Ile Gly Val Pro Gly Ile Gly Val Pro Gly Lys Gly Val Pro Gly
705                 710                 715                 720
Ile Gly Val Pro Gly Ile Gly Glu Glu Ile Gln Ile Gly His Ile Pro
            725                 730                 735
Arg Glu Asp Val Asp Tyr His Leu Tyr Pro Val Pro Gly Ile Gly Val
            740                 745                 750
Pro Gly Ile Gly Val Pro Gly Lys Gly Val Pro Gly Ile Gly Val Pro
            755                 760                 765
Gly Ile Gly Val Gly Val Ala Pro Gly Val Gly Val Ala Pro Gly Val
            770                 775                 780
Gly Val Ala Pro Gly Val Pro Gly Ile Gly Val Pro Gly Ile Gly Val
785                 790                 795                 800
Pro Gly Lys Gly Val Pro Gly Ile Gly Val Pro Gly Ile Gly Glu Glu
                805                 810                 815
Ile Gln Ile Gly His Ile Pro Arg Glu Asp Val Asp Tyr His Leu Tyr
            820                 825                 830
Pro Val Pro Gly Ile Gly Val Pro Gly Ile Gly Val Pro Gly Lys Gly
            835                 840                 845
Val Pro Gly Ile Gly Val Pro Gly Ile Gly Val Gly Val Ala Pro Gly
            850                 855                 860
Val Gly Val Ala Pro Gly Val Gly Val Ala Pro Gly Val
865                 870                 875

<210> SEQ ID NO 4
<211> LENGTH: 352
<212> TYPE: PRT
<213> ORGANISM: Artificial Sequence
<220> FEATURE:
<223> OTHER INFORMATION: Synthetic peptide HSS1

<400> SEQUENCE: 4

Met Glu Ser Leu Leu Pro Val Pro Gly Ile Gly Val Pro Gly Ile Gly
1               5                   10                  15
Val Pro Gly Lys Gly Val Pro Gly Ile Gly Val Pro Gly Ile Gly Val
            20                  25                  30
Pro Gly Ile Gly Val Pro Gly Ile Gly Val Pro Gly Lys Gly Val Pro
        35                  40                  45
Gly Ile Gly Val Pro Gly Ile Gly Asp Asp Asp Glu Glu Lys Phe Leu
    50                  55                  60
Arg Arg Ile Gly Arg Phe Gly Val Pro Gly Ile Gly Val Pro Gly Ile
65                  70                  75                  80
Gly Val Pro Gly Lys Gly Val Pro Gly Ile Gly Val Pro Gly Ile Gly
```

-continued

```
                 85                  90                  95
Val Pro Gly Ile Gly Val Pro Gly Ile Gly Val Pro Gly Lys Gly Val
            100                 105                 110
Pro Gly Ile Gly Val Pro Gly Ile Gly Val Pro Gly Ile Gly Val Pro
            115                 120                 125
Gly Ile Gly Val Pro Gly Lys Gly Val Pro Gly Ile Gly Val Pro Gly
            130                 135                 140
Ile Gly Val Pro Gly Ile Gly Val Pro Gly Ile Gly Val Pro Gly Lys
145                 150                 155                 160
Gly Val Pro Gly Ile Gly Val Pro Gly Ile Gly Asp Asp Asp Glu Glu
            165                 170                 175
Lys Phe Leu Arg Arg Ile Gly Arg Phe Gly Val Pro Gly Ile Gly Val
            180                 185                 190
Pro Gly Ile Gly Val Pro Gly Lys Gly Val Pro Gly Ile Gly Val Pro
            195                 200                 205
Gly Ile Gly Val Pro Gly Ile Gly Val Pro Gly Ile Gly Val Pro Gly
            210                 215                 220
Lys Gly Val Pro Gly Ile Gly Val Pro Gly Ile Gly Val Pro Gly Ile
225                 230                 235                 240
Gly Val Pro Gly Ile Gly Val Pro Gly Lys Gly Val Pro Gly Ile Gly
            245                 250                 255
Val Pro Gly Ile Gly Val Pro Gly Ile Gly Val Pro Gly Ile Gly Val
            260                 265                 270
Pro Gly Lys Gly Val Pro Gly Ile Gly Val Pro Gly Ile Gly Asp Asp
            275                 280                 285
Asp Glu Glu Lys Phe Leu Arg Arg Ile Gly Arg Phe Gly Val Pro Gly
            290                 295                 300
Ile Gly Val Pro Gly Ile Gly Val Pro Gly Lys Gly Val Pro Gly Ile
305                 310                 315                 320
Gly Val Pro Gly Ile Gly Val Pro Gly Ile Gly Val Pro Gly Ile Gly
            325                 330                 335
Val Pro Gly Lys Gly Val Pro Gly Ile Gly Val Pro Gly Ile Gly Val
            340                 345                 350
```

<210> SEQ ID NO 5
<211> LENGTH: 797
<212> TYPE: PRT
<213> ORGANISM: Artificial Sequence
<220> FEATURE:
<223> OTHER INFORMATION: Synthetic peptide HSS3

<400> SEQUENCE: 5

```
Met Glu Ser Leu Leu Pro Val Pro Gly Ile Gly Val Pro Gly Ile Gly
1               5                  10                  15
Val Pro Gly Lys Gly Val Pro Gly Ile Gly Val Pro Gly Ile Gly Val
            20                  25                  30
Pro Gly Ile Gly Val Pro Gly Ile Gly Val Pro Gly Lys Gly Val Pro
            35                  40                  45
Gly Ile Gly Val Pro Gly Ile Gly Asp Asp Asp Glu Glu Lys Phe Leu
            50                  55                  60
Arg Arg Ile Gly Arg Phe Gly Val Pro Gly Ile Gly Val Pro Gly Ile
65                  70                  75                  80
Gly Val Pro Gly Lys Gly Val Pro Gly Ile Gly Val Pro Gly Ile Gly
            85                  90                  95
Val Pro Gly Ile Gly Val Pro Gly Ile Gly Val Pro Gly Lys Gly Val
```

```
            100                 105                 110
Pro Gly Ile Gly Val Pro Gly Ile Gly Val Pro Gly Ile Gly Val Pro
            115                 120                 125

Gly Ile Gly Val Pro Gly Lys Gly Val Pro Gly Ile Gly Val Pro Gly
            130                 135                 140

Ile Gly Val Pro Gly Ile Gly Val Pro Gly Ile Gly Val Pro Gly Lys
145                 150                 155                 160

Gly Val Pro Gly Ile Gly Val Pro Gly Ile Gly Asp Asp Asp Glu Glu
            165                 170                 175

Lys Phe Leu Arg Arg Ile Gly Arg Phe Gly Val Pro Gly Ile Gly Val
            180                 185                 190

Pro Gly Ile Gly Val Pro Gly Lys Gly Val Pro Gly Ile Gly Val Pro
            195                 200                 205

Gly Ile Gly Val Pro Gly Ile Gly Val Pro Gly Ile Gly Val Pro Gly
            210                 215                 220

Lys Gly Val Pro Gly Ile Gly Val Pro Gly Ile Gly Val Pro Gly Ile
225                 230                 235                 240

Gly Val Pro Gly Ile Gly Val Pro Gly Lys Gly Val Pro Gly Ile Gly
            245                 250                 255

Val Pro Gly Ile Gly Val Pro Gly Ile Gly Val Pro Gly Ile Gly Val
            260                 265                 270

Pro Gly Lys Gly Val Pro Gly Ile Gly Val Pro Gly Ile Gly Asp Asp
            275                 280                 285

Asp Glu Glu Lys Phe Leu Arg Arg Ile Gly Arg Phe Gly Val Pro Gly
            290                 295                 300

Ile Gly Val Pro Gly Ile Gly Val Pro Gly Lys Gly Val Pro Gly Ile
305                 310                 315                 320

Gly Val Pro Gly Ile Gly Val Pro Gly Ile Gly Val Pro Gly Ile Gly
            325                 330                 335

Val Pro Gly Lys Gly Val Pro Gly Ile Gly Val Pro Gly Ile Gly Val
            340                 345                 350

Pro Ala Val Gly Val Pro Ala Val Gly Val Pro Ala Val Gly Val Pro
            355                 360                 365

Ala Val Gly Val Pro Ala Val Gly Val Pro Ala Val Gly Val Pro Ala
            370                 375                 380

Val Gly Val Pro Ala Val Gly Val Pro Ala Val Gly Val Pro Ala Val
385                 390                 395                 400

Gly Val Pro Ala Val Gly Val Pro Ala Val Gly Val Pro Ala Val Gly
            405                 410                 415

Val Pro Ala Val Gly Val Pro Ala Val Gly Val Pro Ala Val Gly Val
            420                 425                 430

Pro Ala Val Gly Val Pro Ala Val Gly Val Pro Ala Val Gly Val Pro
            435                 440                 445

Ala Val Gly Val Pro Gly Ile Gly Val Pro Gly Ile Gly Val Pro Gly
            450                 455                 460

Lys Gly Val Pro Gly Ile Gly Val Pro Gly Ile Gly Val Pro Gly Ile
465                 470                 475                 480

Gly Val Pro Gly Ile Gly Val Pro Gly Lys Gly Val Pro Gly Ile Gly
            485                 490                 495

Val Pro Gly Ile Gly Asp Asp Asp Glu Glu Lys Phe Leu Arg Arg Ile
            500                 505                 510

Gly Arg Phe Gly Val Pro Gly Ile Gly Val Pro Gly Ile Gly Val Pro
            515                 520                 525
```

```
                        -continued

Gly Lys Gly Val Pro Gly Ile Gly Val Pro Gly Ile Gly Val Pro Gly
    530                 535                 540
Ile Gly Val Pro Gly Ile Gly Val Pro Gly Lys Gly Val Pro Gly Ile
545                 550                 555                 560
Gly Val Pro Gly Ile Gly Val Pro Gly Ile Gly Val Pro Gly Ile Gly
                565                 570                 575
Val Pro Gly Lys Gly Val Pro Gly Ile Gly Val Pro Gly Ile Gly Val
            580                 585                 590
Pro Gly Ile Gly Val Pro Gly Ile Gly Val Pro Gly Lys Gly Val Pro
        595                 600                 605
Gly Ile Gly Val Pro Gly Ile Gly Asp Asp Asp Glu Glu Lys Phe Leu
    610                 615                 620
Arg Arg Ile Gly Arg Phe Gly Val Pro Gly Ile Gly Val Pro Gly Ile
625                 630                 635                 640
Gly Val Pro Gly Lys Gly Val Pro Gly Ile Gly Val Pro Gly Ile Gly
                645                 650                 655
Val Pro Gly Ile Gly Val Pro Gly Ile Gly Val Pro Gly Lys Gly Val
            660                 665                 670
Pro Gly Ile Gly Val Pro Gly Ile Gly Val Pro Gly Ile Gly Val Pro
        675                 680                 685
Gly Ile Gly Val Pro Gly Lys Gly Val Pro Gly Ile Gly Val Pro Gly
    690                 695                 700
Ile Gly Val Pro Gly Ile Gly Val Pro Gly Ile Gly Val Pro Gly Lys
705                 710                 715                 720
Gly Val Pro Gly Ile Gly Val Pro Gly Ile Gly Asp Asp Asp Glu Glu
                725                 730                 735
Lys Phe Leu Arg Arg Ile Gly Arg Phe Gly Val Pro Gly Ile Gly Val
            740                 745                 750
Pro Gly Ile Gly Val Pro Gly Lys Gly Val Pro Gly Ile Gly Val Pro
        755                 760                 765
Gly Ile Gly Val Pro Gly Ile Gly Val Pro Gly Ile Gly Val Pro Gly
    770                 775                 780
Lys Gly Val Pro Gly Ile Gly Val Pro Gly Ile Gly Val
785                 790                 795
```